US005693522A

United States Patent [19]
Chada et al.

[11] Patent Number: 5,693,522
[45] Date of Patent: Dec. 2, 1997

[54] ANTI-CANCER IMMUNOTHERAPEUTICS

[75] Inventors: Sunil Chada, Vista; Mordechai Bodner, San Diego; Douglas J. Jolly, La Jolla; Jack R. Barber; Caty E. DeJesus, both of San Diego, all of Calif.

[73] Assignee: Chiron Viagene, Inc.

[21] Appl. No.: 371,922

[22] Filed: Jan. 11, 1995

Related U.S. Application Data

[63] Continuation of Ser. No. 104,424, Aug. 9, 1993, abandoned, which is a continuation of Ser. No. 800,328, Nov. 29, 1991, abandoned.

[51] Int. Cl.$^6$ .............................. C12N 15/00; C12N 5/00; C07H 21/02
[52] U.S. Cl. ............................... 435/2.402; 435/172.3; 435/320.1; 536/23.1
[58] Field of Search ............................... 435/320.1, 172.3, 435/240.2

[56] References Cited

U.S. PATENT DOCUMENTS

| | | | |
|---|---|---|---|
| 4,405,712 | 9/1983 | Vande Woude | 435/5 |
| 4,797,368 | 1/1989 | Carter et al. | 435/320.1 |
| 4,861,719 | 8/1989 | Miller | 435/236 |
| 4,871,838 | 10/1989 | Boxx | 536/7 |
| 4,931,275 | 6/1990 | Shinitzky et al. | 424/88 |
| 4,957,859 | 9/1990 | Bizab | 435/7 |
| 4,965,196 | 10/1990 | Levinson | 435/69.1 |
| 4,980,289 | 12/1990 | Temin | 435/325 |

FOREIGN PATENT DOCUMENTS

| | | |
|---|---|---|
| 0 178220 | 4/1986 | European Pat. Off. ........ C12N 15/00 |
| 178 220 | 4/1986 | European Pat. Off. . |
| 0 243204 | 10/1987 | European Pat. Off. ........ C12N 7/00 |
| 243 204 | 10/1987 | European Pat. Off. . |
| 0 293181 | 11/1988 | European Pat. Off. ........ C12N 15/00 |
| 293 181 | 11/1988 | European Pat. Off. . |
| WO 89/01973 | 3/1989 | WIPO . |
| WO 89/02468 | 3/1989 | WIPO . |
| WO 89/05349 | 6/1989 | WIPO . |
| WO 90/02806 | 3/1990 | WIPO . |
| WO 90/11092 | 10/1990 | WIPO . |
| WO 90/14357 | 11/1990 | WIPO . |
| WO 92/07000 | 4/1992 | WIPO . |

OTHER PUBLICATIONS

Kumar et al., *Science*, vol. 248, 1990, pp. 1101–1104.
Hinds et al., *J. Virol.*, vol. 63, 1989, pp. 739–746.
Fearon et al., *Science*, vol. 247, 1990, pp. 49–56.
Ligtenberg et al., *J. Biol. Chem.*, vol. 265, 1990, pp. 5573–5578.
Miller et al., *BioTechnique*, vol. 7, 1989, pp. 980–990.
Jung, "Human T Lymphocytes Recognize a Peptide of Single Point–Mutated Oncogenic ras Proteins," *J. Exp. Med.* 173:273–277 (1991).
Peace, "T Cell Recognition of Transforming Proteins Encoded by Mutated ras Proto–Oncogenes," *J. Immunol.* 146:2059–2065 (1991).
Der, "The ras Family of Oncogenes," in *Oncogenes*, Benz and Liu (eds.), Kluwer Academic Publishers, Boston, 1989, pp. 73–119.
Bishop, "Molecular Themes in Oncogenesis," *Cell* 64:235–248 (1991).
Jerome, "Cytotoxic T–lymphocytes derived from patient with breast adenocarcinoma recognize an epitope present on the protein core of a mucin molecule preferentially expressed by malignant cells," *Cancer Res.* 51:2908–2916 (1991).
Bos, "Prevalence of ras Gene Mutations in Human Colorectal Cancers," *Nature* 327:293–297 (1987).
Hunter, "Cooperation between Oncogenes," *Cell* 64:249–270 (1991).
McMichael, "Cytotoxic T–Cell Immunity to Influenza," *N. Eng. J. Med.* 309:13–17 (1983).
Anderson, "Prospects for human gene therapy using retroviruses," *Science* 226:401–409 (1984).
Morrow, "The prospects for gene therapy in humans," *Ann. N.Y. Acad. Sci.* 265:13–21 (1975).
Bolognesi, "Prospects for treatment of human retrovirus–associated diseases," *Cancer Research (Suppl)* 45:4700s–4705s (1985).
Friedmann, "Expression of a truncated viral trans–activator selectively impedes lytic infection by its cognate virus," *Nature* 335:452–454 (1988).
Zinkernagel, "Anti–viral protection by virus–immune cytotoxic T–cells: infected target cells are lysed before infectious virus progeny is assembled," *J. Exp. Med.* 145:644–651 (1977).
Mulligan, "Mechanisms of p53 loss in human sarcomas," *PNAS* 87:5863–5867 (1990).
Romano, "Identification and characterization of a p53 gene mutation in a human osteosarcoma cell line," *Oncogene* 4:1483–1488 (1989).
Bressac, "Selective G to T mutations of p53 gene in hepatocellular carcinoma from southern Africa," *Nature* 350:429–431 (1991).

(List continued on next page.)

*Primary Examiner*—Suzanne E. Ziska
*Attorney, Agent, or Firm*—Seed & Berry; Norman J. Kruse; Robert P. Blackburn

[57] ABSTRACT

The present invention provides a method of destroying selected tumor cells comprising administering to a warm-blooded animal a vector construct which directs the expression of at least one immunogenic, non-tumorigenic form of an altered cellular component normally associated with the selected tumor cells. Also provided are vector constructs which direct the expression of altered cellular components. Representative altered cellular components include ras*, p53*, Rb*, alter protein encoded by the Wilms' tumor gene, ubiquitin*, mucin*, DCC, APC, MCC, neu, an altered receptor, and bcr/abl. Also provided are recombinant viruses carrying a vector construct, target cells infected with the recombinant virus, and pharmaceutical compositions comprising the recombinant virus and a pharmaceutically acceptable carrier or diluent.

20 Claims, 5 Drawing Sheets

OTHER PUBLICATIONS

Fung, "Structural Evidence for the Authenticity of the Human Retinoblastoma Gene," *Science* 236:1657–1661 (1987).

Bagchi, "Adenovirus E1A Proteins Can Dissociate Heteromeric Complexes Involving the E2F Transcription Factor: A Novel Mechanism for E1A Trans–Activation," *Cell* 62:659–669 (1990).

Shivji, "Multicomponent Differentiation–Regulated Transcription Factors in F9 Embryonal Carcinoma Stem Cells," *Mol. Cell Biol.* 11:1686–1695 (1991).

Shew, "Deletion of a splice donor site ablates expression of the following exon and produces an unphosphorylated RB protein unable to bind SV40 T antigen," *Cell Growth & Diff.* 1:17–25 (1990).

Shew, "C–terminal truncation of the retinoblastoma gene product leads to functional inactivation," *PNAS* 87:6–10 (1990).

Call, "Isolation and Characterization of a Zinc Finger Polypeptide Gene at the Human Chromosome 11 Wilms' Tumor Locus," *Cell* 60:509–520 (1990).

Gessler, "Homozygous, deletion in Wilms' tumors of zinc finger gene identified by chromosomal jumping," *Nature* 343:744–778 (1990).

Haber, "An Internal Deletion within an 11p13 Zinc Finger Gene Contributes to the Development of Wilms' Tumor," *Cell* 61:1257–1269 (1990).

Buckler, "Isolation, Characterization, and Expression of the Murine Wilms' Tumor Gene (WT1) During Kidney Development," *Mol. Cell Biol.* 11:1707–1712 (1991).

Nikitin, "Early mutation of the neu (erbB–2) gene during ethylnitrosourea–induced oncogenesis in the rat Schwann cell lineage," *PNAS* 88:9939–9943 (1991).

Taylor–Papadimitriou, "Report on the First International Workshop on Carcinoma–Associated Mucins," *Int. J. Cancer* 49:1–5 (1991).

Williams, "Introduction of Foreign Genes Into Tissues of Living Mice by DNA–Coated Microprojectiles," *Proc. Natl. Acad Sci. USA* 88:2726–2730 (1991).

Malkin, "Germ Line p53 Mutations in a Familial Syndrome of Breast Cancer, Sarcomas, and Other Neoplasms," *Science* 250:1233–1238 (1990).

Menon, "Chromosome 17p Deletions and p53 gene Mutations Associated with the Formation of Malignant Neurofibrosarcomas in von Recklinghausen Neurofibromatosis," *PNAS* 87:5435–5439 (1990).

Morein, "The iscom: an immunostimulating system," *Immunol. Letters* 25:281–284 (1990).

Rodrigues, "p53 Mutations in Colorectal Cancer," *PNAS* 87:7555–7559 (1990).

Takahashi, "Induction of CD8+ cytotoxic T cells by immunization with purified HIV–1 envelope protein in ISCOMs," *Nature* 344:873–875 (1990).

Acsadi, "Human dystrophin expression in mdx mice after intramuscular injection of DNA constructs," *Nature* 352:815–818 (1991).

Solomon, "Colorectal cancer genes," *Nature* 343:412–414 (1990).

Golumbek, "Treatment of Established Renal Cancer by Tumor Cells Engineered to Secrete Interleukin 4," *Science* 254:713–716 (1990).

Kinzler, "Identification of FAP Locus Genes from Chromosomal 5q21," *Science* 253:661–664 (1991).

Madden, "Transcriptional Repression Mediated by the WT–1 Wilms Tumor Gene Product, " *Science* 253:1550–1553 (1991).

Mafune, "Ubiquitin Hybrid Protein Gene Expression During Human Colon Cancer Progression," *Arch. Surg.* 126:462–466 (1991).

Nishisho, "Mutations of Chromosome 5q21 Genes in FAP and Colorectal Cancer Patients," *Science* 353:665–669 (1991).

Radford, "Cell–Type Specificity of Interferon–Gamma–Mediated HLA Class I Gene Transcription in Human Hematopoietic Tumor Cells," *Blood* 77(9):2008–2015 (1991).

Rosenfeld, "Adenovirus–Mediated Transfer of a Recombinant α1–Antitrypsin Gene to the Lung Epithelium in Vivo," *Science* 252:431–434 (1991).

Schwartz, "Familial Predisposition to Wilms Tumor Does Not Segregate with the WT1 Gene," *Genomics* 10:927–930 (1991).

Stover, "New use of BCG for recombinant vaccines," *Nature* 351:456–460 (1991).

Wang, "Carcinoma Induction following Direct in Situ Transfer of v–Ha–ras into Rat Mammary Epithelial Cells Using Replication–defective Retrovirus Vectors," *Cancer Research* 51:2642–2648 (1991).

Warner, "Induction of HIV–Specific CTL and Antibody Responses in Mice using Retroviral Vector–Transduced Cells," *AIDS Res. & Human Retro.* 7:645–655 (1991).

Van Heyningen, "Wilms' Tumor: Reconciling Genetics and Biology," *Trends in Genetics* 8:16 (1992).

Martin, "Transformation of quail embryo fibroblasts by a retrovirus carrying a normal human c–myc gene," *EMBO Journal* 5:1529–1533 (1986).

Weber, "MHC Class I Gene Expression by Tumors: Immunotherapeutic Implications," *Current Topics in Microbiol. and Immunol.* 137:140–147 (1988).

Linial, "Transfer of Defective Avian Tumor Virus Genomes by a Rous Sarcoma Virus RNA Packaging Mutant," *J. Virol.* 38:380–382 (1981).

Waldholtz, "Studies Find Some Cancer Patients Have Inherited a Genetic Mutation," *Wall Street Journal* (1992).

Tanaka, "Suppression of tumorigenicity in human colon carcinoma cells by introduction of normal chromosomes 5 and 18;" Nature 349:340–342 (1991).

Anderson, "Construction and Isolation of a Transforming Murine Retrovirus Containing the src Gene or Rous Sarcoma Virus," *J. Virol.* 46:594–605 (1983).

Kinzler, "Identification of a Gene Located at Chromosome 5q21 That is Mutated in Colorectal Cancers," *Science* 251:1366–1370 (1991).

Goyette, "Progression of Colorectal Cancer is Associated with Multiple Tumor Suppressor Gene Defects but Inhibition of Tumorogenicity is Accomplished by Correction of Any Single Defect via Chromosome Transfer," *Mol. and Cell. Biol.* 12:1387–1395 (1992).

Nanus, "Transformation of Human Kidney Proximal Tubule Cells by ras–Containing Retroviruses," *J. Exp. Med.* 169:953–972 (1989).

Horowitz, "Point Mutational Inactivation of the Retinoblastoma Anti–Oncogene," *Science* 243:937–940 (1989).

Levine, "The p53 tumour suppressor gene," *Nature* 351:453–456 (1991).

Iggo, "Increased expression of mutant forms of p53 oncogene in primary lung cancel," *Lancet* 335:675–679 (1990).

James, "Mitotic recombination of chromosome 17 in astrocytomas," *PNAS* 86:2858–2862 (1989).

Prosser, "Evidence that p53 behaves as a tumor suppressor gene in sporadic breast tumors," *Oncogene* 5:1573–1575 (1990).

Bartek, "Genetic and immunochemical analysis of a mutant p53 in human breast cancer," *Oncogene* 5:893–899 (1990).

Slamon, "Studies of the HER-2/neu Proto–oncogene in Human Breast and Ovarian Cancer," in *Cancer Cells 7*, Cold Spring Harbor Laboratory, 1989, pp. 371–380.

Girling, "A core protein epitope of the polymorphic epithelial mucin detected by the monoclonal antibody SM-3 is selectively exposed in a range of primary carcinomas," *Int. J. Cancer* 43:1072–1076 (1989).

Takahashi, "p53: A Frequent Target for Genetic Abnormalities in Lung Cancer," *Science* 246:491–494 (1989).

Tepper, "Murine Interleukin–4 Displays Potent Anti–Tumor Activity in Vivo," *Cell* 57:503–512(1989).

Wu, "Targeting Genes: Delivery and Persistent Expression of a Foreign Gene Driven by Mammalian Regulatory Elements in Vivo," *J. Biol. Chem.* 264:16985–16987 (1989).

Xiong, "Sindbis Virus: An Efficient, Broad Host Range Vector for Gene Expression in Animal Cells," *Science* 243:1188–1191 (1989).

Baker, "Suppression of Human Colorectal Carcinoma Cell Growth by Wild–Type p53," *Science* 249:912–915 (1990).

Bookstein, "Suppression of Tumorogenicity of Human Prostate Carcinoma Cells by Replacing a Mutated RB Gene," *Science* 247:712–715 (1990).

Cance, "Altered Expression of the Retinoblastoma Gene Product in Human Sarcomas," *N. Eng. J. Med.* 323:1457–1462 (1990).

Willis, "Retro–secretion of recombinant proteins," *Nature* 340:323–324 (1989).

Altmann, "Cotransfection of I–CAM–1 and HLA–DR reconstitutes human antigen–presenting cell function in mouse L–cells," *Nature* 338:512–514 (1989).

Capella, "Frequency and Spectrum of Mutations at Codons 12 and 13 of the C–K–ras Gene in Human Tumors," *Enviro. Health Perspectives* (In Press) (1990).

Chen, "Genetic Mechanisms of Tumor Suppression by the Human p53 Gene," *Science* 250:1576–1580 (1990).

Cheng, "Frequent Mutations in the p53 Tumor Suppressor Gene in Human Leukemia T–Cell Lines," *Mol. and Cell. Biology* 10:5502–5509 (1990).

Chiba, "Mutations in the p53 Gene are Frequent in Primary, Resected Non–Small Cell Lung Cancer," *Oncogenes* 5:1603–1610 (1990).

Daley, "Induction of Chronic Myelogenous Leukemia in Mice by the P210$^{bcr/abl}$ Gene of the Philadelphia Chromosome," *Science* 247:824–830 (1990).

Ellis, "Key Issues in the Selection of an Expression System for Vaccine Antigens," *J. Med. Vir.* 31:54–58 (1990).

Flexner, "Attenuation and immunogenicity in primates of vaccinia virus recombinants expressing human interleukin–2," *Vaccine* 8:17–21 (1990).

Gansbacher, "Retroviral Vector–Mediated γ–Interferon Gene Transfer into Tumor Cells Generates Potent and Long Lasting Antitumor Immunity," *Cancer Research* 50:7820–7825 (1990).

Gansbacher, "Interleukin 2 Gene Transfer into Tumor Cells Abrogates Tumorigenicity and Induces Protective Immunity," *J. Exp. Med.* 172:1217–1224 (1990).

Gendler, "Molecular Cloning and Expression of Human Tumor–Associated Polymorphic Epithelial Mucin," *J. Biol. Chem.* 265:15286–15293 (1990).

Hareuveni, "A Transcribed Gene, containing a Variable Number of Tandem Repeats, Codes for a Human Epithelial Tumor Antigen," *Eur. J. Biochem.* 189:475–486 (1990).

Hareuveni, "Vaccination against Tumor Cells Expressing Breast Cancer Epithelial Tumor Antigen," *PNAS* 87:9498–9502 (1990).

Lan, "Cloning and Sequencing of a Human Pancreatic Tumor Mucin cDNA," *J. Biol. Chem.* 265:15294–15299 (1990).

Largaespada, "The Activity of an ABL–MYC Retrovirus in Fibroblast Cell Lines and in Lymphocytes," *Current Topics in Micro & Immun.* 166:91–96 (1990).

Nunez, "Growth– and Tumor–Promoting Effects of Deregulated BLC2 in Human B–Lymphoblastoid Cells," *Proc. Natl. Acad. Sci USA* 86:4589–4593 (1989).

Souyri, "Oncogenicity of Human N–ras Oncogene and Proto–Oncogene Introduced into Retroviral Vectors," *J. Virology* 63(9):3844–3928 (1989).

Watanabe, "Exogenous Expression of Mouse Interferon γcDNA in Mouse Neutoblastoma C1300 Cells Results in Reduced Tumorigenicity by Augmented Anti–Tumor Immunity," *Proc. Natl. Acad Sci. USA* 86:9456–9460 (1989).

MacKay, "Allele Loss on Short Arm of Chromosome 17 in Breast Cancers," *Lancet* Dec.:1384–1385 (1988).

Felgner, "Lipofection: A highly efficient, lipid–mediated DNA–transfection procedure," *PNAS* 84:7413–7417 (1987).

Fisher–Hoch, "Protection of Rhesus Monkeys from Fatal Lassa Fever by Vaccination with a recombinant Vaccinia with a Recombinant Vaccinia Virus Containing the Lassa Virus Glycoprotein Gene," *PNAS* 86:317–321 (1989).

Moss and Flexner, "Vaccinia Virus Expression Vectors," *Ann. N.Y. Acad. of Sci.* 569:86–103 (1989).

Kelman, "Rearrangements in the p53 Gene Philadelphia Chromosome Positive Chronic Myelogenous Leukemia," *Blood* 74:2318–2324 (1989).

Kit, "Recombinant–Derived Modified–Live Herpes virus Vaccines," *Adv. Exp. Med. Biol.* 251:219–236 (1988).

Koike, "Transgenic Mouse Model for Human Gastric Carcinoma," *PNAS* 86:5615–5619 (1989).

Leduc, "Loss of Heterozygosity in a Gene Coding for a Thyroid Hormone Receptor in Lung Cancers," *Am. J. Hum. Genet.* 44:282–287 (1989).

Luytjes, "Amplification, expression and packaging of a foreign gene by influenza virus," *Cell* 59:1107–1113 (1989).

Nigro, "Mutations in the p53 Gene Occur in Diverse Human Tumor Types," *Nature* 342:705–708 (1989).

Gregoriadis, "Liposomes as Immunological adjuvants: antigen incorporation studies," *Vaccine* 5:145–151 (1987).

Samulski, "Helper–Free Stocks of Recombinant Adeno–Associated Viruses: Normal Integration Does Not Require Viral Gene Expression," *J. Vir.* 63:3822–3828 (1989).

Edelman, "Morphoregulatory molecules," *Biochem.* 27:3533–3543 (1988).

Bargmann, "Oncogenic activation of the neu–encoded receptor protein by point mutation and deletion," *EMBO J.* 7:2043–2052 (1988).

Shtivelman, "Alternative Splicing of RNAs Transcribed from the Human abl Gene and From the bcr–abl Fused Gene," *Cell* 47:277–284 (1986).

Flexner, "Successful vaccination with a polyvalent live vector despite existing immunity to an expressed antigen," *Nature* 335:259–262 (1988).

Lee, "Inactivation of the Retinoblastoma Susceptibility Gene in Human Breast Cancer," *Science* 241:218–221 (1988).

Mendelson, "Expression and Rescue of a Nonselected Marker from an Integrated AAV Vector," *Virology* 166:154–165 (1988).

Moore, "Introduction of Soluble Protein into the Class I Pathway of Antigen Processing and Presentation," *Cell* 54:777–785 (1988).

Baker, "Chromosome 17 Deletions and p53 Gene Mutations in Colorectal Carcinomas," *Science* 244:217–221 (1989).

Berman, "Expression and Immunogenicity of the Extracellular Domain of the Human Immunodeficiency Virus Type 1 Envelope Glycoprotein, gp160," *J. Virology* 63:3489–3498 (1989).

Deres, "In vivo priming of virus–specific cytotoxic T lymphocytes with synthetic lipopeptide vaccine," *Nature* 342:561–564 (1989).

Ben–Neriah, "The chronic myelogenous leukemia–specific p210 protein is the product of the bcr/abl hybrid gene," *Science* 233:212–214 (1986).

Quaife, "Pancreatic neoplasia induced by ras expression in acinar cells of transgenic mice a comparable elastase–myc construct produces no pancreatic tumors in transgenic mice," *Cell* 48:1023–1034 (1987).

Staerz, "Cytotoxic T lymphocytes against a soluble protein," *Nature* 329:449–451 (1987).

Wang, "pH–sensitive immunoliposomes mediate target–cell–specific delivery and controlled expression of a foreign gene in mouse," *PNAS* 84:7851–7855 (1987).

Bisceglie, "Hepatocellular Carcinoma," *Ann. of Int. Med.* 108:390–401 (1988).

Friend, "A human DNA segment with properties of the gene that predisposes to retinoblastoma and osteosarcoma," *Nature* 323:643–646 (1986).

Coussens, "Tyrosine Kinase receptor with extensive homology to EGF receptor shares chromosomal location with neu oncogene," *Science* 230:1132–1139 (1985).

Shtivelman, "Fused transcript of abl and bcr genes in chronic myelogenous leukaemia," *Nature* 315:550–554 (1985).

McAleer, "Human hepatitis B vaccine from recombinant yeast," *Nature* 307:178–180 (1984).

Stewart, "Spontaneous Mammary Adenocarcinomas in Transgenic Mice that Carry and Express MTV/myc Fusion Genes," *Cell* 38:627–637 (1984).

Levenbook, "Tumorigenicity Testing of Primate Cell Lines in Nude Mice, Muscle Organ Culture and for Colony Formation in Soft Agarose," *J. Biol. Std.* 13:135–141 (1985).

Schechter, "The neu Oncogene: an erb–B–related Gene Encoding a 185,000–$M_r$ Tumour Antigen," *Nature* 312:513–516 (1984).

Dubensky, "Direct transfection of viral and plasmid DNA into the liver or spleen of mice," *PNAS* 81:7529–7533 (1984).

Shih, "Transforming genes of carcinomas and neuroblastomas introduced into mouse fibroblasts," *Nature* 290:261–264 (1981).

Burrel, "Expression in *Escherichia coli* of hepatitis B virus DNA sequences cloned in plasmid pBR322," *Nature* 279:43–47 (1979).

Mulligan, "Synthesis of rabbit β–globin in cultured monkey kidney cells following infection with a SV40 β–globin recombinant genome," *Nature* 277:108–114 (1979).

Yap, "Transfer of specific cytotoxic T lymphocytes protects mice inoculated with influenza virus," *Nature* 273:238–239 (1978).

Giovanella, "Development of Invasive Tumors in the Nude Mouse after Injection of Cultured Human Melanoma Cells," *J. Natl. Cancer Inst.* 48:1531–1533 (1972).

Chanock, "Immunization by Selective Infection with Type 4 Adenovirus Grown in Human Diploid Tissue Culture," *JAMA* 195:151–158 (1966).

Sanders et al., "Introduction of Foreign Genes Into Tissues of Living Mice by DNA–Coated Microprojectiles," *Proc. Natl. Acad. Sci. USA* 88:2762730.

Call, "Isolation and Characterization of a Zinc Finger Polypeptide Gene at the Human Chromosome 11 Wilms' Tumor Locus," *Cell* 60:509–520 (1991).

Gessler, "Homozygous deletion in Wilms' tumors of zinc finger gene identified by chromosomal jumping," *Nature* 343:744 (1991).

Haber, "An Internal Deletion within an 11p13 Zinc Finger Gene Contributes to the Development of Wilms' Tumor," *Cell* 61:1257–1269 (1991).

Kinzler, "Identification of FAP Locus Genes from Chromosomal 5q21 ," *Science* 253:661–664 (1990).

Madden, "Transcriptional Repression Mediated by the WT–1 Wilms' Tumor Gene Product," *Science* 253:1550–1553 (1990).

Mafune, "Ubiquitin Hybrid Protein Gene Expression During Human Colon Cancer Progression," *Arch. Surg.* 126:462–466 (1990).

Radford, "Cell–Type Specificity of Interferon–Gamma–Mediated HLA Class I Gene Transcription in Human Hematopoietic Tumor Cells," *The Amer. Soc. Hepat.* 9:2008–2015 (1990).

Rosenfeld, "Adenovirus–Mediated Transfer of a Recombinant al–Antitrypsin Gene to the Lung Epithelium in Vivo," *Science* 252:431–434 (1990).

Schwartz, "Familial Predisposition to Wilms' Tumor Does Not Segregate with the WT1 Gene," *Genomics* 10:927–930 (1990).

Stover, "New use of BCG for recombinant vaccines," *Nature* 351:456–458 (1990).

Wang, "Carcinoma Induction following Direct in Situ Transfer of v–Ha–ras into Rat Mammary Epithelial Cells Using Replication–defective Retrovirus Vectors," *Cancer Research* 51:2642–2648 (1990).

Warner "Induction of HIV–Specific CTL and Antibody Responses in Mice using Retroviral Vector–Transduced Cells," *IDS Res. & Human Retro.* 7:645–655 (1990).

Van Heyningen, "Wilms' Tumor: Reconciling Genetics and Biology," *TIG* 8:16 (1990).

Martin, "Transformation of quail embryo fibroblasts by a retrovirus carrying a normal human c–myc gene," *EMBO* 5:1529–1533 (1990).

Weber, "MHC Class 1 Gene Expression by Tumors: Immunotherapeutic Implications," *Current Topics in Microbiol. and Immunol.* 137:140–147 (1990).

Linial, "Transfer of Defective Avian Tumor Virus Genomes by a Rous Sarcoma Virus RNA Packaging Mutant," *J. Virol.* 38:380–382 (1990).

Waldholtz, "Studies Find Some Cancer Patients Have Inherited a Genetic Mutation," *Wall Street Journal* (1990).

Tanaka, "Suppression of tumorigenicity in human colon carcinoma cells by introduction of normal chromosomes 5 and 18," *Nature* 349:340–342 (1990).

Anderson, "Construction and Isolation of a Transforming Murine Retrovirus Containing the src Gene or Rous Sarcoma Virus," *J. Virol.* 46:594–605 (1990).

Kinzler, "Identification of a Gene Located at Chromosome 5q21 That is Mutated in Colorectal Cancers," *Science* 251:1366–1370 (1990).

Goyette, "Progression of Colorectal Cancer is Associated with Multiple Tumor Suppressor Gene Defects but Inhibition of Tumorogenicity is Accomplished by Correction of Any Single Defect via Chromosome Transfer," *Mol. and Cell. Biol.* 12:1387–1315 (1990).

Nanus, "Transformation of Human Kidney Proximal Tubule Cells by ras–Containing Retroviruses," *J. Exp. Med.* 169:953–972 (1990).

Horowitz, "Point Mutational Inactivation of the Retinoblastoma Anti–Oncogene," *Science* 243:937–940 (1990).

Levine, "The p53 tumour suppressor gene," *Nature* 351:453–456 (1990).

James,"Mitotic recombination of chromosome 17 in astrocytomas," *PNAS* 86:2858–2862 (1990).

Baker, "Suppression of Human Colorectal Carcinoma Cell Growth by Wild–Type p53," *Science* 249:912–915 (1989).

Bookstein, "Suppression of Tumorogenicity of Human Prostate Carcinoma Cells by Replacing a Mutated RB Gene," *Science* 247:712–715(1989).

Cance, "Altered Expression of the Retinoblastoma Gene Product in Human Sarcomas," *N. Eng. J. Med.* 323:1457–1462 (1989).

Altmann, "Cotransfection of I–CAM–1 and HLA–DR reconstitutes human antigen–presenting cell function in mouse L–cells," *Nature* 338:512–514 (1989).

Capella, "Frequency and Spectrum of Mutations at Codons 12 and 13 of the C–K–ras Gene in Human Tumors," *Enviro. Health Perspectives* (In Press) (1989).

Chen, "Genetic Mechanisms of Tumor Suppression by the Human p53 Gene," *Science* 250:1576–1580 (1989).

Cheng, "Frequent Mutations in the p53 Tumor Suppressor Gene in Human Leukemia T–Cell Lines," *Mol. and Cell. Biology* 10:5502–5509 (1989).

Chiba, "Mutations in the p53 Gene are Frequent in Primary, Resected Non–Small Cell Lung Cancer," *Oncogenes* 5:1603–1610 (1989).

Daley "Induction of Chronic Myelogenous Leukemia in Mice by the P210bcr/abl Gene of the Philadelphia Chromosome," *Science* 247:824–830 (1989).

Ellis, "Key Issues in the Selection of an Expression System for Vaccine Antigens," *J. Med. Vir.* 31:54–58 (1989).

Flexner, "Attenuation and immunogenicity in primates of vaccinia virus recombinants expressing human interleukin–2," *Vaccine* 8:17–21 (1989).

Gansbacher, "Retroviral Vector–Mediated Gamma–Interferon Gene Transfer into Tumor Cells Generates Potent and Long Lasting Antitumor Immunity," *Cancer Research* 50:7820–7825 (1989).

Gansbacher, "Interleukin 2 Gene Transfer into Tumor Cells Abrogates Tumorigenicity and Induces Protective Immunity," *J. Exp. Med.* 172:1217–1224 (1989).

Gendler, "Molecular Cloning and Expression of Human Tumor–Associated Polymorphic Epithelial Mucin," *J. Biol. Chem.* 265:15286–15293 (1989).

Hareuveni, "A Transcribed Gene, containing a Variable Number of Tandem Repeats, Codes for a Human Epithelial Tumor Antigen," *Eur. J. Biochem.* 789:475–486 (1989).

Hareuveni, "Vaccination against Tumor Cells Expressing Breast Cancer Epithelial Tumor Antigen," *PNAS* 67:9498–9502 (1989).

Lan, "Cloning and Sequencing of a Human Pancreatic Tumor Mucin cDNA," *J. Biol. Chem.* 265:15294–15299 (1989).

Largaespada, "The Activity of an ABL–MYC Retrovirus in Fibroblast Cell Lines and in Lymphocytes," *Current Topics in Micro & Immun.* 166:91–96 (1989).

Nunez et al. "Growth– and Tumor–Promoting Effects of Deregulated BLCI in Human G–Lymphoblastoid Cells," *Proc. Natl. Acad. Sci USA* 86:4589–4593 (1989).

Felgner, "Lipofection: A highly efficient, lipid–mediated DNA–transfection procedure," *PNAS* 84:7413–7417 (1988).

Fisher–Hoch, "Protection of Rhesus Monkeys from Fatal Lassa Fever by Vaccination with a recombinant Vaccinia with a Recombinant Vaccinia Virus Containing the Lassa Virus Glycoprotein Gene," *PNAS* 86:317–321 (1988).

Flexner "Vaccinia Virus Expression Vectors," *Ann. N.Y. Acad. of Sci.* 569:86–103 (1988).

Kelman, "Rearrangements in the p53 Gene Philadelphia Chromosome Positive Chronic Myelogenous Leukemia," *Blood* 74:2318–2324 (1988).

Leduc, "Loss of Heterozygosity in a Gene Coding for a Thyroid Hormone Receptor in Lung Cancers," *Am. J. Hum. Genet.* 44:282–287 (1988).

Luytjes, "Amplification, expression and packaging of a foreign gene by influenza virus," *Cell* 59:1107–1113 (1988).

Nigro, "Mutations in the p53 Gene Occur in Diverse Human Tumor Types," *Nature* 342:705–708 (1988).

Gregortadis, "Nato ASI: Immunological adjuvants and vaccines," *Vaccine* 5:145–151 (1988).

Samulski, "Helper–Free Stocks of Recombinant Adeno–Associated Viruses: Normal Integration Does Not Require Viral Gene Expression," *J. Vir.* 63:3822–3828 (1988).

Edelman, "Morphoregulatory molecules," *Biochem.* 27:3533–3543 (1988).

Shtivelman et al., "Alternative Splicing of RNAs Transcribed from the Human abl Gene and From the bcr–abl Fused Gene," *Cell* 47:277–284 (1988).

Flexner, "Successful vaccination with a polyvalent live vector despite existing immunity to an expressed antigen," *Nature* 335:259–262 (1987).

Lee, "Inactivation of the Retinoblastoma Susceptibility Gene in Human Breast Cancer," *Science* 241:219–221 (1987).

Mendelson, "Expression and Rescue of a Nonselected Marker from an Integrated AAV Vector," *Virology* 166:154–165 (1987).

Moore, "Introduction of Soluble Protein into the Class I Pathway of Antigen Processing and Presentation," *Cell* 54:777–785 (1987).

Baker, "Chromosome 17 Deletions and p53 Gene Mutations in Colorectal Carcinomas," *Science* 244:217–221 (1987).

Berman "Expression and Immunogenicity of the Extracellular Domain of the Human Immunodeficiency Virus Type 1 Envelope Glycoprotein, gp160," *J. Virology* 63:3489–3498 (1987).

Deres, "In vivo priming of virus–specific cytotoxic T lymphocytes with synthetic lipopeptide vaccine," *Nature* 342:561–564(1987).

Quaife, "Pancreatic neoplasia induced by ras expression in acinar cells of transgenic mice a comparable elastase–myc construct produces no pancreatic tumors in transgenic mice," *Cell* 48:1023–1034 (1986).

Staerz, "Cytotoxic T lymphocytes against a soluble protein," *Nature* 329:449–451 (1986).

Wang, "pH-sensitive immunoliposomes mediate target-cell-specific delivery and controlled expression of a foreign gene in mouse," *PNAS* 84:7851–7855 (1986).

Bisceglie, "Hepatocellular Carcinoma," *Ann. of Int. Med.* 108:390–401 (1986).

Levenbook, "Tumorigenicity Testing of Primate Cell Lines in Nude Mice, Muscle Organ Culture and for Colony Formation in Soft Agarose," *J. Biol. Std.* 13:135–141 (1984).

Dubiensky, "Direct transfection of viral and plasmid DNA into the liver or spleen of mice," *PNAS* 81:7529–7533 (1983).

Liglenby et al *JBC* 265(10):5573, 1990.

Hends et al *J F Virology* 63(2):739, 1989.

Hirds et al *J. of Virology* 63(2): 739, 1989.

Robin et al Cancer 7, 1989, CSH in Molecular Diagnosis of Human Cancer.

Salgaller et al., "Expression of a Native (180KD) and Deleted Form (70KD) of the Human Carcinoembryonic Antigen Following Transduction of a Mouse Adenocarcinoma Cell Line (Meeting Abstract)," *Proc. Ann. Meet. Am. Assoc. Cancer Res* 32:A1622 (1991).

Hareuveni et al., "Vaccinia Recombinants Expressing Secreted and Transmembrane Forms of Breast Cancer-Associated Epithelial Tumour Antigen (ETA)," *Vaccine* 9:618–626 (1991).

Lathe et al. "Antitumor Immunity:Exploration of Vaccination In Breast Cancer (Meeting Abstract)," *Bienn. Int. Breast Canc. Res. Conf.* (1989).

McKenzie et al. "Induction of Antitumor Immunity by Immunization with a Vaccinia Virus Vector Expressing an Oncogene-encoded Product," *Vaccines* 88:19–23 (1988).

Shiu–Lok Hu et al., "Recombinant Vaccinia Virus Expressing the Human Melanoma–associated Antigen p97 as a Therapeutic Anti–tumor Vaccine," *Vaccines* 88:47–52 (1988).

Hill et al., "Mutant p53—A Target for Cytotoxic T Lymphocytes? (Meeting Abstract)," *ICRF, Inst. of Molecular Medicine* (1991).

Jolly et al., "Retroviral Vectors as Vaccines and Immunotherapeutics," *Semin Immunol* 2(5):329–39 (1990).

Rabin et al., "Expression of ras and neu Oncogene Proteins as Determined by Monoclonal Antibodies," *Cancer Cells* 7:157–160 (1989).

ANTI-CANCER IMMUNOTHERAPEUTICS

CROSS-REFERENCE TO RELATED APPLICATION

This application is a continuation of U.S. patent application Ser. No. 08/104,424, filed Aug. 9, 1993, now abandoned, which was a continuation of U.S. patent application Ser. No. 07/800,328, filed Nov. 29, 1991, now abandoned.

TECHNICAL FIELD

The present invention relates generally to the field of anti-cancer immunotherapy, and more specifically, to methods of killing selected tumor cells, by generating an immune response against the tumor cells.

BACKGROUND OF THE INVENTION

Cancer accounts for one-fifth of the total mortality in the United States, and is the second leading cause of death. Cancer is typically characterized by the uncontrolled division of a population of cells. This uncontrolled division typically leads to the formation of a tumor, which may subsequently metastasize to other sites.

Primary solid tumors can generally be treated adequately by surgical resection. However, the majority of patients which present with solid tumors also possess micrometastases beyond the primary tumor site. If treated with surgery alone, approximately 70% of these patients will experience recurrence of the cancer. In addition to surgery, many cancers are now also treated with a combination of therapies involving cytotoxic chemotherapeutic drugs (e.g., vincristine, vinblastine, cisplatin, etc.) and/or radiation therapy. One difficulty with this approach, however, is that radiotherapeutic and chemotherapeutic agents are toxic to normal tissues, and often create life-threatening side effects. In addition, these approaches often have extremely high failure/remission rates (up to 90% depending upon the type of cancer).

In addition to chemo- and radiation therapies, many have attempted to bolster or augment an individual's own immune system in order to eliminate the cancer cells. Several immunotherapies have utilized bacterial or vital components in order to stimulate the immune system to destroy the tumor cells. Examples of such components include immunomodulatory agents (such as BCG, endotoxin, and mixed bacterial vaccines), interferons ($\alpha$, $\beta$, and $\gamma$), interferon inducers (e.g., *Brucella abortus*, and various viruses), and thymic factors (e.g., thymosin fraction 5, and thymosin alpha-1) (see generally "Principles of Cancer Biotherapy," Oldham (ed.), Raven Press, New York, 1987). Such agents have generally been useful as adjuvants and as nonspecific stimulants in animal tumor models, but have not yet proved generally effective in humans.

Lymphokines have also been utilized in the treatment of cancer. Briefly, lymphokines are secreted by a variety of cells, and generally have an effect on specific cells in the generation of an immune response. Examples of lymphokines include Interleukins (IL)-1, -2, -3, and -4, as well as colony stimulating factors such as G-CSF, GM-CSF, and M-CSF. Recently, one group has utilized IL-2 to stimulate peripheral blood cells in order to expand and produce large quantities of cells which are cytotoxic to tumor cells (Rosenberg et al., *N. Engl. J. Med.* 323:1485–1492, 1985).

Others have suggested the use of antibody-mediated anti-cancer therapies. Briefly, antibodies may be developed which recognize certain cell surface antigens that are either unique, or more prevalent on cancer cells compared to normal cells. These antibodies, or "magic bullets," may be utilized either alone or conjugated with a toxin in order to specifically target and kill tumor cells (Dillman, "Antibody Therapy," *Principles of Cancer Biotherapy*, Oldham (ed.), Raven Press, Ltd., New York, 1987). For example, Ball et al. (*Blood* 62:1203–1210, 1983) treated several patients with acute myelogenous leukemia with one or more of several monoclonal antibodies specific for the leukemia, resulting in a marked decrease in circulating leukemia cells during treatment. Similarly, others have used toxin-conjugated antibodies therapeutically to treat a variety of tumors, including, for example, melanomas, colorectal carcinomas, prostate carcinomas, breast carcinomas, and lung carcinomas (see Dillman, supra). One difficulty however, is that most monoclonal antibodies are of murine origin, and thus hypersensitivity against the murine antibody may limit its efficacy, particularly after repeated therapies. Common side effects include fever, sweats and chills, skin rashes, arthritis, and nerve palsies.

Therefore, agents which can augment natural host defences against tumor induction or progression may increase remission rates and enhance survival of patients, without the cytotoxic side effects of prior methods. The present invention provides such agents, and further provides other related advantages.

SUMMARY OF THE INVENTION

The present invention provides methods for destroying selected tumor cells with an altered cellular component which is normally associated with the selected tumor cells. Within one aspect, a method is provided for destroying selected tumor cells comprising the step of administering to a warm-blooded animal a vector construct which directs the expression of at least one immunogenic, non-tumorigenic form of an altered cellular component normally associated with the selected tumor cells. Within another aspect of the invention, a method is provided for destroying selected tumor cells in a warm-blooded animal comprising the steps of (a) removing cells from a warm-blooded animal, (b) administering to the removed cells a vector construct which directs the expression of at least one immunogenic, non-tumorigenic form of an altered cellular component normally associated with the selected tumor cells, and (c) returning the cells to a warm-blooded animal, such that the selected tumor cells are destroyed. As will be evident to one of ordinary skill in the art, the animal from which the cells are removed need not be the same animal to which they are returned, although preferably, they should be histocompatible. In addition, it should be understood that within the context of the present invention when reference is made to a viral construct which "expresses" any substance in a cell, that this in fact refers to protein production of the resulting provirus following reverse transcription of the viral RNA into the cell. Within various embodiments of the invention, the vector construct may be carried by a recombinant retrovirus, or by a recombinant virus selected from the group consisting of adeno-associated virus, canary pox virus, adenovirus, and pox virus.

Within another aspect of the present invention, a vector construct is provided which directs the expression of at least one immunogenic, non-tumorigenic form of an altered cellular component. Within various embodiments, the cellular component may be altered by a point mutation, by a deletion, or by a chromosomal translocation. Within other embodiments, the altered cellular components include, ras*, p53*, Rb*, altered protein encoded by the Wilms' tumor gene, ubiquitin*, mucin*, DCC, APC, MCC, neu, an altered receptor, or polypeptides resulting from chromosomal translocations such as bcr/abl. Within another embodiment, non-tumorigenic altered cellular components are provided, including for example, $\Delta ras^{*12}$, $\Delta ras^{*13}$, and $\Delta ras^{*61}$. Also provided are vector constructs which direct the expression of several altered cellular components, including, for example, a vector construct which directs the expression of both ras* and p53, or a vector construct which directs the expression or ras*, mucin*, and DCC.

Within another aspect of the invention, recombinant retroviruses as well as other recombinant viruses, such as adeno-associated viruses, canary pox viruses, adenoviruses, and pox viruses, are provided for carrying the above-described vector constructs. Target cells infected with these recombinant viruses are also provided, including, for example, embodiments wherein the target cells are selected from the group consisting of human, macaque, dog, rat, and mouse cells.

Also provided are pharmaceutical compositions comprising the above-described recombinant viruses, in combination with a pharmaceutically acceptable carrier or diluent.

These and other aspects of the present invention will become evident upon reference to the following detailed description and attached drawings.

DETAILED DESCRIPTION OF THE INVENTION

Figure 1:
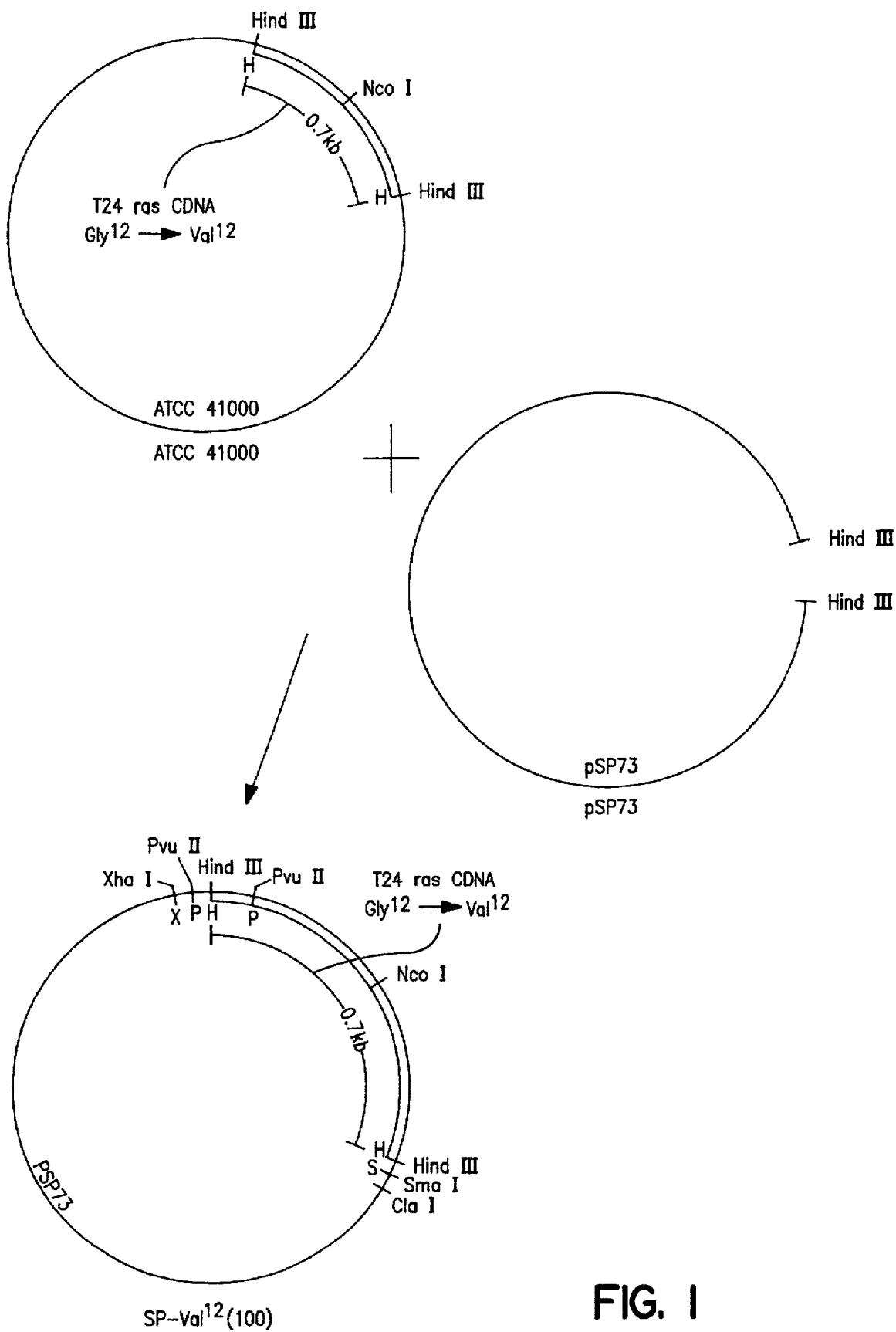
FIG. 1 is a schematic illustration which outlines the construction of the plasmid SP-Val$^{12}$(100).

Prior to setting forth the invention, it may be helpful to an understanding thereof to first set forth definitions of certain terms that will be used hereinafter.

"Altered Cellular Component" refers to proteins and other cellular constituents which are either associated with rendering a cell tumorigenic, or are associated with tumorigenic cells in general but are not required or essential for rendering the cell tumorigenic. Before alteration, the cellular components may be essential to normal cell growth and regulation, and include for example, proteins which regulate intracellular protein degradation, transcriptional regulation, cell-cycle control, and cell-cell interaction. After alteration, the cellular components no longer perform their regulatory functions, and hence the cell may experience uncontrolled growth. Representative examples of altered cellular components include ras*, p53*, Rb*, altered protein encoded by the Wilms' tumor gene, ubiquitin*, mucin*, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described in more detail below, as well as discussed in cited references. All references which have been cited below are hereby incorporated by reference in their entirety.

"Non-tumorigenic" refers to altered cellular components which will not cause cellular transformation or induce tumor formation in nude mice. Representative assays which distinguish tumorigenic cellular components from non-tumorigenic cellular components are described in more detail below and in Example 4.

"Immunogenic" as utilized within the present invention refers to altered cellular components which are capable, under the appropriate conditions, of causing an immune response. This response must be cell-mediated and may also include a humoral response. Representative assays which may be utilized to determine immunogenicity are described in more detail below and in Example 5.

"Vector construct" refers to an assembly which is capable of expressing the sequence(s) or gene(s) of interest. The vector construct must include promoter elements and preferably includes a signal that directs polyadenylation. In addition, the vector construct must include a sequence which, when transcribed, is operably linked to the sequence (s) or gene(s) of interest and acts as a translation initiation sequence. Preferably, the vector construct may also include a selectable marker such as Neo, SV$_2$ Neo, TK, hygromycin, phleomycin, histidinol, or DHFR, as well as one or more restriction sites and a translation termination sequence. In addition, if the vector construct is placed into a retrovirus, the vector construct must include a packaging signal.

As noted above, the present invention provides methods and compositions suitable for destroying selected tumor cells. Within one aspect of the present invention, a method is provided which comprises the step of administering to a warm-blooded animal a vector construct which directs the expression of at least one immunogenic, non-tumorigenic form of an altered cellular component normally associated with the selected tumor cells. Within another aspect of the invention, a method is provided for destroying selected tumor cells in a warm-blooded animal comprising the steps of (a) removing cells from a warm-blooded animal, (b) administering to the removed cells a vector construct which directs the expression of at least one immunogenic, non-tumorigenic form of an altered cellular component normally associated with the selected tumor cells, and (c) returning the cells to a warm-blooded animal, such that the selected tumor cells are destroyed. In this manner, an immune response is generated which destroys tumor cells which are associated with the altered cellular component.

Briefly, the ability to recognize and defend against foreign pathogens is central to the function of the immune system. This system, through immune recognition, is capable of distinguishing "self" from "nonself" (foreign), which is essential to ensure that defensive mechanisms are directed towards invading entities rather than against host tissues. The fundamental features of the immune system are the presence of highly polymorphic cell surface recognition structures (receptors) and effector mechanisms (antibodies and cytolytic cells) for the destruction of invading pathogens.

Cytolytic T lymphocytes (CTL) are normally induced by the display of processed pathogen-specific peptides in conjunction with MHC molecules along with accessory molecules such as CD3, ICAM-1, ICAM-2, LFA-1, or analogs thereof (e.g., Altmann et al., Nature 338:512, 1989). Other genes coding for proteins that enhance the stimulation or recognition of cell mediated responses may also be used in this context. Antigenic peptide presentation in association with MHC (major histocompatibility) Class I molecules leads to CD8+ CTL production. Peptides presented in association with MHC Class II molecules leads to production of antibodies, helper cells and B-cell memory and may induce CD4+ CTLs. The methods which are described in greater detail below provide an effective means of inducing potent class I-restricted protective and therapeutic CTL responses, as well as humoral responses.

As noted above, altered cellular components refers to proteins and other cellular constituents which are either associated with rendering the cell tumorigenic, or are associated with tumorigenic cells in general, but are not required or essential for rendering the cell tumorigenic. Representative examples of alterations which occur in cellular components include point mutations, deletions, and chromosomal translocations. These alterations serve to generate an altered cellular component which the host immune system may not recognize as "self," and thereby eliminate the neoplastic or pre-neoplastic cells containing the altered cellular component.

Within one embodiment of the present invention, a vector construct is provided which directs the expression of a non-tumorigenic, altered ras (ras*) gene. Briefly, the ras* gene is an attractive target because it is causally linked to the neoplastic phenotype, and indeed may be necessary for the induction and maintenance of tumorigenesis in a wide variety of distinct cancers, such as pancreatic carcinoma, colon carcinoma and lung adenocarcinoma. In addition, ras* genes are found in pre-neoplastic tumors, and therefore immune intervention therapy may be applied prior to detection of a malignant tumor.

Normal ras genes are non-tumorigenic and ubiquitous in all mammals. They are highly conserved in evolution and appear to play an important role in maintenance of the cell cycle and normal growth properties. The normal ras protein is a G-protein which binds GTP and has GTPase activity, and is involved in transmitting signals from the external milieu to the inside of the cell, thereby allowing a cell to respond to its environment. Ras* genes on the other hand alter the normal growth regulation of neoplastic cells by uncoupling cellular behavior from the environment, thus leading to the uncontrolled proliferation of neoplastic cells. Mutation of the ras gene is believed to be an early event in carcinogenesis (Kumar et al., "Activation of ras Oncogenes Preceding the Onset of Neoplasia," *Science* 248:1102–1104, 1990), which, if treated early, may prevent tumorigenesis.

Ras* genes occur in a wide variety of cancers, including for example, pancreatic, colon, and lung adenocarcinomas (see Table 1 below).

TABLE 1

| Tumor type | Incidence of ras mutations |
|---|---|
| Pancreatic Adenocarcinoma | 90% |
| Colon Adenoma | 50% |
| Colon Adenocarcinoma | 50% |
| Seminoma | 40% |
| Lung Adenocarcinoma | 30% |
| Myelodisplatic Syndrome | 30% |
| Acute Myelogenous leukemia | 30% |
| Keratinoacanthoma | 30% |
| Thyroid carcinoma | 25% |
| Melanomas | 20% |
| Bladder carcinoma | 6% |

The spectrum of mutations occurring in the ras genes found in a variety of cancers is quite limited. These mutations alter the GTPase activity of the ras protein by converting the normal on/off switch to a constitutive ON position. Tumorigenic mutations in ras* occur primarily (in vivo) in only 3 codons: 12, 13 and 61. Codon 12 mutations are the most prevalent in both human and animal tumors. Table 2 below sets forth the incidence of mutations at codons 12 and 13 for various human tumors.

TABLE 2

| | Approximate percentage of specific mutations at codons 12 and 13 of ras* | | | | | | |
|---|---|---|---|---|---|---|---|
| Tumor type/Mutation | GAT Asp | GAC Asp | AGT Ser | CGT Arg | TGT Cys | GTT Val | GCT Ala |
| Pancreatic Carcinoma | 47% | 2% | 2% | 10% | 12% | 27% | <1% |
| Colorectal Adenoma or Carcinoma | 39% | 23% | 3% | <1% | 9% | 23% | 2% |
| Lung Carcinoma | 17% | 4% | 4% | 4% | 40% | 30% | <1% |

Table 3 summarizes known in vivo mutations (codons 12, 13 and 61) which activate human ras, as well as potential mutations which have in vitro transforming activity. Potential mutations with in vitro transforming activity were produced by the systematic substitution of amino acids for the normal codon (e.g., other amino acids were substituted for the normal glycine at position 12). Such mutations, while not presently known to occur in humans or animals, may serve as the basis for an anti-cancer immunotherapeutic if they are eventually found to arise in vivo.

TABLE 3

| Amino acid substitutions that activate human ras proteins | | | | | | | |
|---|---|---|---|---|---|---|---|
| Amino Acid Mutant Codon | Gly 12 | Gly 13 | Ala 59 | Gln 61 | Glu 63 | Asn 116 | Lys 117 | Asp 119 |
| In vivo | Val Arg Asp Cys Ala Ser Phe | Asp Val Arg | | Arg His Leu | | | | |
| In vitro | Ala Asn Gln Glu His Ile Leu Lys Met Phe Ser Thr Trp Tyr | Ser | Thr | Val Ala Cys Asn Ile Met Thr Tyr Trp Phe Gly | Lys | His Ile | Glu Arg | His Glu Ala Asn |

Alterations as described above result in the production of proteins containing novel coding sequence(s). The novel proteins encoded by these sequence(s) may be used as a marker of tumorigenic cells, and an immune response directed against these novel coding regions may be utilized to destroy tumorigenic cells containing the altered sequences (ras*).

Within another embodiment of the present invention, a vector construct is provided which directs the expression of an altered p53 (p53*) gene. Briefly, p53 is a nuclear phosphoprotein which was originally discovered in extracts of transformed cells, and thus was initially classified as an oncogene (Linzer and Levine, *Cell* 17:43–52, 1979; Lane and Crawford, *Nature* 278:261–263, 1979). It was later discovered that the original p53 cDNA clones were mutant forms of p53 (Hinds et al., *J. Virol.* 63:739–746, 1989). It now appears that p53 is a tumor suppressor gene, which negatively regulates the cell cycle, and that mutation of this gene may lead to minor formation. Of colon carcinomas that have been studied, 75%–80% show a loss of both p53 alleles, one through deletion, and the other through point mutation. Similar mutations are found in lung cancer, and in brain and breast tumors.

The majority of p53 mutations (e.g., p53$^{*1}$, p53$^{*2}$, etc.) are clustered between amino-acid residues 130 to 290 (see Levine et al., *Nature* 351:453–456, 1991; see also the following references which describe specific mutations in more detail: Baker et al., *Science* 244:217–221, 1989; Nigro et al., *Nature* 342:705–708, 1989 (p53 mutations cluster at four "hot spots" which coincide with the four highly conserved regions of the genes and these mutations are observed in human brain, breast, lung and colon tumors); Vogelstein, *Nature* 348:681–682, 1990; Takahashi et al., *Science* 246:491–494, 1989; Nigro et al., *Lancet* 335:675–679, 1990; James et al., *Proc. Natl. Acad. Sci. USA* 86:2858–2862, 1989; Mackay et al., *Lancet* 11:1384–1385, 1988; Kelman et al., *Blood* 74:2318–2324, 1989; Malkin et al., *Science* 250:1233–1238, 1990; Baker et al., *Cancer Res.* 50:7717–7722, 1991; Chiba et al., *Oncogene* 5:1603–1610, 1990 (pathogenesis of early stage non-small cell lung cancer is associated with somatic mutations in the p53 gene between codons 132 to 283); Prosser et al., *Oncogene* 5:1573–1579, 1990 (mutations in the p53 gene coding for amino acids 126 through 224 were identified in primary breast cancer); Cheng and Hass, *Mol. Cell. Biol.* 10:5502–5509, 1990; Bartek et al., *Oncogene* 5:893–899, 1990; Rodrigues et al., *Proc. Natl. Acad. Sci. USA* 87:7555–7559, 1990; Menon et al., *Proc. Natl. Acad. Sci. USA* 87:5435–5439, 1990; Mulligan et al., *Proc. Natl. Acad. Sci. USA* 87:5863–5867, 1990; and Romano et al., *Oncogene* 4:1483–1488, 1990 (identification of a p53 mutation at codon 156 in human osteosarcoma derived cell line HOS-SL)).

Certain alterations of the p53 gene may be due to certain specific toxins. For example, Bressac et al. (*Nature* 350:429–431, 1991) describes specific G to T mutations in codon 249, in patients affected with hepatocellular carcinoma. One suggested causative agent of this mutation is aflatoxin B$_1$, a liver carcinogen which is known to be a food contaminant in Africa.

Four regions of the gene that are particularly affected occur at residues 132–145, 171–179, 239–248, and 272–286.

Three "hot spots" of particular interest occur at residues 175, 248 and 273 (Levine et al., *Nature* 351:453–456, 1991). These alterations as well as others which are described above result in the production of protein(s) which contain novel coding sequence(s). The novel proteins encoded by these sequences may be used as a marker of tumorigenic cells, and an immune response directed against these novel coding regions may be utilized to destroy tumorigenic cells containing the altered sequence (p53*).

Within another embodiment of the present invention, a vector construct is provided which directs the expression of an altered Rb (Rb*) gene. Briefly, retinoblastoma is a childhood eye cancer associated with the loss of a gene locus designated Rb, which is located in chromosome band 13q14. A gene from this region has been cloned which produces a nuclear phosphoprotein of about 110 kd (Friend et al., *Nature* 323:643, 1986; Lee et al., *Science* 235:1394, 1987; and Fung et al., *Science* 236:1657, 1987).

Rb is believed to be a negative regulator of cellular proliferation, and has a role in transcriptional control and cell-cycle regulation. Rb binds to at least seven proteins found in the nucleus, and in particular, appears to be involved with a cellular transcription factor which has been designated both E2F (Bagchi et al., *Cell* 62:659–669, 1990) and DRTF (Shivji and La Thangue, *Mol. Cell. Biol.* 11:1686–1695, 1991). Rb is believed to restrict cellular growth by sequestering a variety of nuclear proteins involved in cellular proliferation.

Deletions within the Rb gene have been detected which evidence that the Rb gene may be responsible for tumorigenicity. These deletions include, for example, a deletion in exon 21 in a prostate cancer and bladder cancer cell line (Bookstein et al., *Science* 247:712–715, 1990; Horowitz et al., *Science* 243:937, 1989), a deletion of exon 16 in a small-cell carcinoma of the lung (Shew et al., *Cell Growth and Diff.* 1:17, 1990), and a deletion between exons 21 and 27 (Shew et al., *Proc. Natl. Acad. Sci. USA* 87:6, 1990). Deletion of these exons results in the production of a protein containing a novel coding sequence at the junction of the deleted exons. This novel protein coding sequence may be used as a marker of tumorigenic cells, and an immune response directed against this novel coding region may eliminate tumorigenic cells containing the Rb exon deletion.

Within another embodiment of the present invention, a vector construct is provided which directs the expression of an altered gene which causes Wilms' tumor. Briefly, Wilms' tumor is typically found in children younger than 16 years of age. One child in 10,000 will develop this minor, which comprises approximately 5% of childhood cancers. The tumor usually presents itself as a large abdominal mass which is surrounded by a fibrous pseudocapsule. Approximately 7% of the tumors are multifocal in one kidney, and 5.4% are involved with both kidneys. The Wilms' tumor gene has been localized to chromosome 11p13, and a cDNA clone (wt1) has been isolated that is characteristic of a tumor suppressor gene (Call et al., *Cell* 60:509, 1990; Gessler et al., *Nature* 343:774–778, 1990; Rose et al., *Cell* 60:495, 1990; and Haber et al., *Cell* 61:1257, 1990). The wt1 gene encodes a protein which contains four zinc fingers and a glutamine and proline rich amino terminus. Such structures are believed to be associated with transcriptional and regulatory functions.

Mutations of the Wilms' tumor gene include the insertion of lysine, threonine, and serine between the third and forth zinc fingers. A wt1 protein which contains such insertions does not bind to the EGR-1 site. A second alternative mutation results in the insertion of about 17 amino acids in the region immediately NH$_2$-terminal to the zinc finger domain (Madden et al., *Science* 253:1550–1553, 1991; Call et al., *Cell* 60:509, 1990; Gessler et al., *Nature* 343:774–778, 1990; Rose et al., *Cell* 60:495, 1990; Haber et al., *Cell* 61:1257, 1990; and Buckler et al., *Mol. Cell. Biol.* 11:1707, 1991).

Alterations as described above result in the production of protein(s) containing novel coding sequence(s). The novel protein(s) encoded by these sequence(s) may be used as a marker of tumorigenic cells, and an immune response directed against these novel coding region(s) may be utilized to destroy tumorigenic cells containing the altered sequence (s) or gene(s), which cause Wilms' tumor.

Within another embodiment of the present invention, a vector construct is provided which directs the expression of an altered mucin. Mucins are large molecular weight glycoproteins which contain approximately 50% carbohydrate.

Polymorphic epithelial mucin (PEM) is a tumor-associated mucin (Girling et al., *Int. J. Cancer* 43:1072–1076, 1989) which is found in the serum of cancer patients. The full-length cDNA sequence has been identified (Gendler et al., *J. Biol Chem.* 265(25):15286–15293, 1990; Lan et al., *J. Biol. Chem.* 265(25):15294–15299, 1990; and Ligtenberg et al., *J. Biol. Chem.* 265:5573–5578, 1990). Breast tumors and pancreatic tumors both express a mucin with an identical core sequence, containing a 20 amino-acid tandem repeat (Jerome et al., *Cancer Res.* 51:2908–2916, 1991). CTL lines which have been developed to breast minors which cross-react with pancreatic tumor targets, and further appear to specifically recognize the specific 20 amino-acid tandem repeat (Jerome et al., supra). A sequence encoding one or more of the 20 amino-acid tandem repeats may be expressed by a vector construct of the present invention, in order to develop an immune response against tumor cells which contain this sequence.

Within another embodiment of the present invention, a vector construct is provided which directs the expression of an altered DCC (deleted in colorectal carcinomas) gene. Briefly, a very common region of allelic loss in colorectal tumors is chromosome 18q, which is lost in more than 70% of carcinomas, and in almost 50% of late adenomas. A presumptive tumor suppressor gene (DCC) from this region has been identified (Fearon et al., 1990), which encodes a protein with significant homology to cell-surface adhesion molecules, such as neural cell-adhesion molecule (NCAM) and contactin (reviewed by Edelman in *Biochem* 27:3533–3543, 1988). This protein is believed to play a role in the development of colorectal tumors, perhaps through alterations in normal cell-cell and/or cell-extracellular matrix interactions.

The DCC gene is expressed in normal colonic mucosa, but its expression is reduced or absent in the majority of colorectal carcinomas (Solomon, *Nature* 343:412–414, 1990). This loss of expression has been associated in some cases with somatic mutations of the DCC gene. A contiguous stretch of DNA comprising 370 kb has been cloned which encodes an approximately 750 amino add protein (Fearon et al., "Identification of a Chromosome 18q Gene That Is Altered in Colorectal Cancers," *Science* 247:49–56, 1990).

Within another embodiment of the present invention, a vector construct is provided which directs the expression of MCC or APC. Both MCC (mutated in colorectal cancer) and APC have been identified as tumor suppressor genes (Kinzler et al., *Science* 251:1366–1370, 1991) which undergo mutation in familial adenomatous polyposis (FAP). FAP is believed to be the most common autosomal dominant disease which leads to cancer, and it affects at least 1 in 5,000 individuals in the United States (Nishiho et al., *Science* 358:665–669, 1991). Affected individuals usually develop hundreds to thousands of adenomatous polyps of the colon and rectum, which may progress to carcinoma. Gardner's syndrome ("GS," a variant of FAP) presents desmoid tumors, osteomas, and other neoplasms together with multiple adenomas of the colon and rectum. This proliferation is believed to be induced by loss or inactivation of the familial adenomatous polyposis gene (and in particular, MCC and APC) which is found on chromosome 5q.

For example, in Nishiho et al. (supra), the following germ line mutations of the APC gene were found in FAP and GS patients: (1) Codon 280, a serine to stop mutation (in a patient with mandibular osteoma), (2) codon 302, an arginine to stop mutation in two separate patients, one with a desmoid tumor, (3) codon 414, an arginine to cysteine mutation in a patient with mandibular osteoma, and (5) codon 713, a serine to stop mutation in another patient with mandibular osteoma (Nishiho et al., *Science* 353:665–669, 1991). In addition, six point mutations were identified in MCC codon numbers 12, 145, 267, 490, 506, and 698, as well as an additional 4 somatic mutations in APC (codons number 289, 332, 438, and 1338).

Alterations as described above result in the production of protein(s) containing novel coding sequence(s). The novel protein(s) encoded by these sequence(s) may be used as a marker of tumorigenic cells, and an immune response directed against these novel coding region(s) may be utilized to destroy tumorigenic cells containing the altered sequence (s) or gene(s) which cause DCC, APC, or MCC.

Within another embodiment of the present invention, a vector construct is provided which directs the expression of altered ubiquitin. Briefly, ubiquitin is a cellular protein which is involved in cell-cycle control and DNA replication. Other functions of ubiquitin include intracellular protein degradation, heat-shock response, transcriptional regulation, cell-cycle control, and cell-cell interaction. Ubiquitin is believed to be a marker molecule that targets proteins for a variety of metabolic fates, and a cDNA sequence which encodes this protein has been identified (Redman et al., "Nucleotide sequence analysis of a cDNA encoding human ubiquitin reveals that ubiquitin is synthesized as a precursor," *J. Biol. Chem.* 263:4926–4931, 1988).

A mutant ubiquitin (ubiquitin*) has recently been identified in a human colon carcinoma cell line (Mafune et al., *Arch.-Surg.* 126:462–466, 1991). This tumor cell contains a novel fusion protein consisting of a hybrid ubiquitin-ribosomal protein S27a. The fusion junction of this protein results in a novel nonself protein sequence which may be immunogenic, and therefore used to eliminate tumor cells carrying this fusion protein.

Within another embodiment of the present invention, a vector construct is provided which directs the expression of altered bcr/abl. Briefly, in tumor cells from almost all patients with chronic myelogenous leukemia, the Philadelphia chromosome, a fusion of chromosomes 9 and 22, directs the synthesis of the fused $P210^{bcr/abl}$ protein. This hybrid gene encodes a 210 kD phosphoprotein with disregulated protein-kinase activity which leads to the chronic myelogenous leukemia (Daley et al., *Science* 247:824–829, 1990; Shtivelman et al., *Nature* 315:550–554, 1985; Ben-Neriah et al., *Science* 233:212–214, 1986; and Shtivelman et al., *Cell* 47:277–284, 1986). The fusion junction of these two chromosomes results in a novel nonself protein sequence which may be immunogenic, and thus used to eliminate tumor cells carrying this fusion protein.

Within other embodiments of the invention, a vector construct is provided which directs the expression of an altered receptor which is functionally locked or stuck in an "ON" or "OFF" mode. Briefly, many cellular receptors are involved in cell growth by monitoring the external environment and signalling the cell to respond appropriately. If either the monitoring or signalling mechanisms fail, the cell will no longer respond to the external environment and may exhibit uncontrolled growth. Many different receptors or receptor-like structures may function as altered cellular components, including, for example, neu and mutated or altered forms of the thyroid hormone receptor, the PDGF receptor, the insulin receptor, the Interleukin receptors (e.g., IL-1, -2, -3, etc. receptors), or the CSF receptors, such as the G-CSF, GM-CSF, or M-CSF receptors.

For example, neu (also referred to as the Human Epidermal Growth Factor Receptor "HER" or the Epidermal Growth Factor "EGF" receptor) is an altered receptor which is found in at least 28% of women with breast cancer. A cDNA clone which encodes this protein has been isolated (Slamon et al., *Science* 244:707–712, 1989; Slamon et al., *Cancer Cells* 7:371–380, 1989; Shih et al., *Nature* 290:261, 1981). This done encodes a protein that has extracellular, transmembrane, and intracellular domains (Schechter, *Nature* 312:513, 1984; Coussens et al., *Science* 230:1138–1139, 1985) and thus is believed to encode the neu receptor.

Studies of the rat neu gene isolated from chemically induced neuroglioblastoma cells indicate that it contains a single mutation at position 664 from valine to glutamic acid (Bargmann et al., *EMBO J.* 7:2043, 1988). In other studies, baby rats which were treated with N-ethyl-N-nitrosourea developed malignant tumors of the nervous system. All 47 trigeminal schwannomas and 12 neurinomas which developed carried a T to A transversion at position 664 of the neu gene (Nikitin et al., *Proc. Natl. Acad. Sci USA* 88:9939–9943, 1991).

Other altered receptors may also be expressed by vector constructs in order to destroy selected tumor cells. For example, a deletion in chromosome 3p21-p25 has been associated with small-cell lung carcinomas (Leduc et al., *Am. J. Hum. Genet.* 44:282–287, 1989). A deletion is believed to occur in the ERBAβ gene which otherwise codes for a DNA-binding thyroid hormone receptor (THR).

Alterations in receptors as described above result in the production of protein(s) (or receptors) containing novel coding sequence(s). The novel protein(s) encoded by these sequence(s) may be used as a marker of tumorigenic cells, and an immune response directed against these novel coding region(s) may be utilized to destroy tumorigenic cells containing the altered sequence(s) or gene(s).

Sequences which encode the above-described altered cellular components may be obtained from a variety of sources. For example, plasmids which contain sequences that encode altered cellular products may be obtained from a depository such as the American Type Culture Collection (ATCC, Rockville, Md.), or from commercial sources such as Advanced Biotechnologies (Columbia, Md.). Representative examples of plasmids coming some of the above-described sequences include ATCC No. 41000 (containing a G to T mutation in the 12th codon of ras), and ATCC No. 41049 (containing a G to A mutation in the 12th codon).

Alternatively, plasmids which encode normal cellular components may also be obtained from depositories such as the ATCC (see, for example, ATCC No. 41001 which contains a sequence which encodes the normal ras protein, ATCC No. 57103 which encodes abl; and ATCC Nos. 59120 or 59121 which encode the bcr locus) and mutated to form the altered cellular component. Methods for mutagenizing particular sites may readily be accomplished using methods known in the art (see Sambrook et al., supra., 15.3 et seq.). In particular, point mutations of normal cellular components such as ras may readily be accomplished by site-directed mutagenesis of the particular codon, for example, codons 12, 13 or 61.

In like manner, sequences which encode normal cellular components may be obtained from cells, and mutated by site-directed mutagenesis in order to obtain sequences which encode the altered cellular component. Such sequences may be readily obtained by, for example, preparing primers on either side of the sequence, and amplifying the sequence by PCR (see U.S. Pat. Nos. 4,683,202; 4,683,195; and 4,800, 159) (see also PCR *Technology: Principles and Applications for DNA Amplification*, Erlich (ed.), Stockton Press, 1989). Briefly, double-stranded DNA is denatured by heating in the presence of heat stable Taq polymerase, specific DNA primers, ATP, CTP, GTP and TTP. Double-stranded DNA is produced when synthesis is complete. This cycle may be repeated many times, resulting in a factorial amplification of the desired DNA.

Sequences which encode altered cellular components may also be synthesized, for example, on an Applied Biosystems Inc. DNA synthesizer (e.g., ABI DNA synthesizer model 392 (Foster City, Calif.). Such sequences may be ligated to form a long single-stranded DNA molecule. Briefly, short, overlapping antisense linkers are mixed with the primary sequences, after which the primary sequences may be ligated to form a long, single-stranded DNA molecule.

Once a sequence encoding the altered cellular component has been obtained, it is necessary to ensure that the sequence encodes a non-tumorigenic protein. Various assays are known and may easily be accomplished which assess the tumorigenicity of a particular cellular component. Representative assays include a rat fibroblast assay (which is described in more detail below in Example 4), tumor formation in nude mice or rats, colony formation in soft agar, and preparation of transgenic animals, such as transgenic mice.

Tumor formation in nude mice or rats is a particularly important and sensitive method for determining the tumorigenicity of a particular cellular component. Nude mice lack a functional cellular immune system (i.e., do not possess CTLs), and therefore provide a useful in vivo model in which to test the tumorigenic potential of cells. Normal non-tumorigenic cells do not display uncontrolled growth properties if infected into nude mice. However, transformed cells will rapidly proliferate and generate tumors in nude mice. Briefly, in one embodiment the vector construct is administered to syngeneic murine cells, followed by injection into nude mice. The mice are visually examined for a period of 2 to 8 weeks after injection in order to determine tumor growth. The mice may also be sacrificed and autopsied in order to determine whether tumors are present. (Giovanella et al., *J. Natl. Cancer Inst.* 48:1531–1533, 1972; Furesz et al., "Tumorigenicity testing of cell lines considered for production of biological drugs," *Abnormal Cells, New Products and Risk*, Hopps and Petricciani (eds.), Tissue Culture Association, 1985; and Levenbook et al., *J. Biol. Std.* 13:135–141, 1985).

Tumorigenicity may also be assessed by visualizing colony formation in soft agar (Macpherson and Montagnier, *Vir.* 23:291–294, 1964). Briefly, one property of normal non-tumorigenic cells is "contact inhibition" (i.e., cells will stop proliferating when they touch neighboring cells). If cells are plated in a semi-solid agar support medium, normal cells rapidly become contact inhibited and stop proliferating, whereas tumorigenic cells will continue to proliferate and form colonies in soft agar.

Transgenic animals, such as transgenic mice, may also be utilized to assess the tumorigenicity of an altered cellular component. (Stewart et al., *Cell* 38:627–637, 1984; Quaife et al., *Cell* 48:1023–1034, 1987; and Koike et al., *Proc. Natl. Acad. Sci. USA* 86:5615–5619, 1989). In transgenic animals, the gene of interest may be expressed in all tissues of the animal. This dysregulated expression of the transgene may serve as a model for the tumorigenic potential of the newly introduced gene.

If the altered cellular component is associated with making the cell tumorigenic, then, it is necessary to make the altered cellular component non-tumorigenic. For example, within one embodiment, the sequence or gene of interest which encodes the altered cellular component is truncated in order to render the gene product non-tumorigenic. The gene encoding the altered cellular component may be truncated to a variety of sizes, although it is preferable to retain as much as possible of the altered cellular component. In addition, it is necessary that any truncation leave intact at least some of the immunogenic sequences of the altered cellular component. Alternatively, multiple translational termination codons may be introduced into the gene which encodes the altered cellular component, downstream of the immunogenic region. Insertion of termination codons will prematurely terminate protein expression, thus preventing expression of the transforming portion of the protein.

Within one embodiment, the ras* gene is truncated in order to render the ras* protein non-tumorigenic. Briefly, the carboxy-terminal amino acids of ras* functionally allow the protein to attach to the cell membrane. Truncation of these sequences renders the altered cellular component non-tumorigenic. Preferably, the ras* gene is truncated in the purine ring formation, for example around the sequence which encodes amino acid number 110. The ras* gene sequence may be truncated such that as little as about 20 amino acids (including the altered amino acid(s) are encoded by the vector construct, although preferably, as many amino acids as possible should be expressed (while maintaining non-tumorigenicity).

Within another embodiment, the p53* protein is modified by truncation in order to render the cellular component non-tumorigenic. As noted above, not all mutations of the p53 protein are tumorigenic, and therefore, not all mutations would have to be truncated. Nevertheless, within a preferred embodiment, p53* is truncated to a sequence which encodes amino acids 100 to 300, thereby including all four major "hot spots."

Other altered cellular components which are oncogenic may also be truncated in order to render them non-tumorigenic. For example, both neu and bcr/abl may be truncated in order to render them non-tumorigenic. Non-tumorigenicity may be confirmed by assaying the truncated altered cellular component as described above, or as described in Example 4.

It should be noted, however, that if the altered cellular component is only associated with non-tumorigenic cells in general, and is not required or essential for making the cell tumorigenic, then it is not necessary to render the cellular component non-tumorigenic. Representative examples of such altered cellular components which are not tumorigenic include Rb*, ubiquitin*, and mucin*.

As noted above, in order to generate an appropriate immune response, the altered cellular component must also be immunogenic. Immunogenicity of a particular sequence is often difficult to predict, although T cell epitopes often possess an immunogenic amphipathic alpha-helix component. In general, however, it is preferable to determine immunogenicity in an assay. Representative assays include an ELISA which detects the presence of antibodies against the newly introduced vector, as well as assays which test for T helper cells such as gamma-interferon assays, IL-2 production assays, and proliferation assays. A particularly preferred method for determining immunogenicity is the CTL assay which is described in detail below in Example 5.

As noted above, within another aspect of the present invention, several different altered cellular components may be co-expressed in order to form a general anti-cancer therapeutic. Generally, it will be evident to one of ordinary skill in the art that a variety of combinations can be made. Within preferred embodiments, this therapeutic may be targeted to a particular type of cancer. For example, nearly all colon cancers possess mutations in ras, p53, DCC APC or MCC genes. A vector construct which co-expresses a number of these altered cellular components may be administered to a patient with colon cancer in order to treat all possible mutations. This methodology may also be utilized to treat other cancers. Thus, a vector construct which co-expresses mucin*, ras*, neu, and p53* may be utilized to treat breast cancer.

Once a particular altered cellular component has been selected, it is placed into a vector construct which directs its expression. Vector constructs of the present invention may be used as an alternative to surgery, or may be used in combination with surgical or adjuvant modalities, and may prove more effective post-surgically then chemotherapy or radiotherapy since a specific cytotoxicity against remaining tumor cells is elicited. Construction of retroviral vector constructs is described in greater detail below in Example 2. In addition, construction of additional vector constructs as well as administration of retroviral constructs by direct injection is described in greater detail in an application entitled "Recombinant Retroviruses" (U.S. Ser. No. 07/586, 603, filed Sept. 21, 1990). This application is incorporated by reference in its entirety.

Other viruses may also be utilized to administer vector constructs, including, for example, poliovirus (Evans et al., *Nature* 339:385–388, 1989, and Sabin, *J. of Biol. Standardization* 1:115–118, 1973); rhinovirus; adeno-associated viruses and adeno viruses (Berkner, *Biotechniques* 6:616–627, 1988); pox viruses, such as the canary pox virus or the vaccinia virus (Fisher-Hoch et al., *PNAS* 86:317–321, 1989, and Flexner et al., *Ann. N.Y. Acad. Sci.* 569:86–103, 1989; Flexner et al., *Vaccine* 8:17–21, 1990; SV40 (Mulligan et al., *Nature* 277:108–114, 1979); influenza virus (Luytjes et al., *Cell* 59:1107–1113, 1989; McMicheal et al., *The New England Journal of Medicine* 309:13–17, 1983; and Yap et al., *Nature* 273:238–239, 1978); adenovirus (Berkner, *Biotechniques* 6:616–627, 1988, and Rosenfeld et al., *Science* 252:431–434, 1991); adenoassociated virus (Samulski et al., *Journal of Virology* 63:3822–3828, 1989, and Mendelson et al., *Virology* 166:154–165, 1988); herpes (Kit, *Adv. Exp. Med. Biol.* 215:219–236, 1989); and sindbis virus (Xiong et al., *Science* 234:1188–1191, 1989).

Various methods may be utilized to administer the vector construct, or nucleic acids which encode the altered cellular component to patients directly, including, for example, transfection by methods utilizing various physical methods, such as lipofection (Felgner et al., *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991); liposomes (Wang et al., *PNAS* 84:7851–7855, 1987); CaPO$_4$ (Dubensky et al., *PNAS* 81:7529–7533, 1984); or DNA ligand (Wu et al, *J. of Biol. Chem.* 264:16985–16987, 1989).

In addition, a CTL response may also be generated by administration of a bacteria which expresses the altered cellular component(s) on its cell surface. Representative examples include BCG (Stover, *Nature* 351:456–458, 1991) and salmonella (Newton et al., *Science* 244:70–72, 1989).

Cell mediated and humoral responses may also be induced against tumors by parenteral administration of the altered cellular components themselves. Briefly, altered cellular components (ras*, p53*, etc.) or peptides carrying relevant epitopes can be produced in a number of known ways (Ellis and Gerety, *J. Med. Virol.* 31:54–58, 1990), including chemical synthesis (Bergot et al., *Applied Biosystems Peptide Synthesizer User Bulletin No.* 16, 1986, Applied Biosystems, Foster City California) and DNA expression in recombinant systems, such as the insect-derived baculovirus system (Doerfler, *Current Topics in Immunology* 131:51–68, 1986), mammalian-derived systems (such as CHO cells) (Berman et al., *J. Virol.* 63:3489–3498, 1989), yeast-derived systems (McAleer et al., *Nature* 307:178–180), and prokaryotic systems (Burrel et al., *Nature* 279:43–47, 1979).

The proteins or peptides can be purified by conventional means and delivered by a number of methods to induce cell-mediated responses, including class I and class II responses. These methods include use of adjuvants of various types, such as ISCOMS (Morein, *Immunology Letters* 25:281–284, 1990; Takahashi et al., *Nature* 344:873–875m, 1990), liposomes (Gergoriadis et al., *Vaccine* 5:145–151, 1987), lipid conjugation (Deres et al., *Nature* 342:561–564, 1989), coating of the peptide on autologous cells (Staerz et al., *Nature* 329:449–451, 1987), pinosomes (Moore et al., *Cell* 54:777–785, 1988), alum, complete or incomplete Freund's adjuvants (Hart et al., *Proc. Natl. Acad. Sci. USA* 88:9448–9452, 1991), or various other useful adjuvants (e.g., Allison and Byars, *Vaccines* 87:56–59, Cold Spring Harbor Laboratory, 1987) that allow effective parenteral administration.

Alternatively, the proteins or peptides corresponding to altered cellular components can be encapsidated for oral administration to elicit immune response in enteric capsules (Channock et al., *J. Amer. Med. Assoc.* 195:445–452, 1966) or other suitable carriers, such as poly (DL-lactide-co-glycolate) spheres (Eldridge et al. in *Proceedings of the International Conference on Advances in AIDS Vaccine Development*, DAIDS, NIAID, U.S. Dept of Health & Human Services, 1991), for gastrointestinal release.

In addition, the proteins or peptides can be manipulated to render them more immunogenic (e.g., by adding amino acid sequences that correspond to T helper epitopes), to promote cellular uptake by adding hydrophobic residues, to particulate structures, or any combination of these (Hart, op. cit., Milich et al., *Proc. Natl. Acad. Sci. USA* 85:1610–1614, 1988; Willis, *Nature* 340:323–324, 1989; Griffiths et al., *J. Virol.* 65:450–456, 1991).

Within one aspect of the invention, a method is provided for destroying selected tumor cells in a warm-blooded animal comprising the steps of (a) removing cells from a warm-blooded animal, (b) administering to the removed cells a vector construct which directs the expression of at least one immunogenic, non-tumorigenic form of an altered cellular component normally associated with the selected tumor cells, and (c) returning the cells to a warm-blooded animal, such that said selected tumor cells are destroyed. Within the context of the present invention it should be understood that the removed cells need not necessarily be returned to the same animal, but may be utilized to destroy selected tumor cells in another animal. In such a case it generally preferable to have histocompatibility matched animals. In addition, it should be understood that a variety of cells (target cells) may be utilized within the context of the present invention, including for example, human, macaque, dog, rat, and mouse cells.

Cells may be removed from a variety of locations, including for example from the skin (dermal fibroblasts) and the blood (peripheral blood leukocytes). If desired, particular fractions of cells such as a T cell subset or stem cells may also be removed from the blood for administration of the vector construct (e.g., PCT WO 91/16116, an application entitled "Immunoselection Device and Method"). Vector constructs may then be administered to the removed cells utilizing any of the above-described techniques, followed by the return of the cells to the warm-blooded animal.

Within another aspect of the present invention, a vector construct is provided which directs the expression of a tumorigenic cellular component and a prodrug activator. For example, within one embodiment, an altered cellular component and a prodrug activator, such as Herpes Simplex Virus Thymidine Kinase (HSVTK), are incorporated into the vector construct. This vector construct is then administered to cells in the presence of an exogenous substance, such as acyclovir, which kills cells that express the HSVTK.

Prior to administering the vector construct, it may first be desirable to determine what altered cellular component(s) are associated with the tumor cells. This may be determined in a number of ways. For example, ELISA-based assays may be utilized to detect specific minor markers or altered cellular components.

Alternatively, presence of an altered cellular component may also be determined on a genetic level. For example, DNA or cDNA may be obtained directly from a tumor and subjected under hybridizing conditions with a labeled probe specific for the altered cellular component. If the number of minor cells is small, PCR (as described above) may be utilized to amplify selected nucleic acid regions, which may then similarly be subjected to hybridization with the labeled probe. The hybridization probe should be selected and utilized under conditions which allow it to specifically bind to the sequence which encodes the altered cellular component. In addition, it should be recognized that one of ordinary skill in the art could readily apply other detection methods to the native or amplified nucleic acids, including, for example, use of the RNase A mismatch cleavage method (Lopez-Galindez et al., *Proc. Natl. Acad. Sci. USA* 85:3522–3526, 1988).

Within preferred embodiments of the present invention, pharmaceutical compositions are provided comprising one of the above described recombinant viruses, such as a recombinant retrovirus or recombinant virus selected from the group consisting of adeno-associated virus, canary pox virus, adenovirus, and pox virus, or a recombinant DNA vector with or without attached ligands, in combination with a pharmaceutically acceptable carrier or diluent. The composition may be prepared either as a liquid solution, or as a solid form (e.g., lyophilized) which is suspended in a solution prior to administration. In addition, the composition may be prepared with suitable carriers or diluents for either injection, oral, or rectal administration. Generally, the recombinant virus will constitute approximately 0.25% to 25% of the composition, and preferably about 5% to 20%.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris pH=7.2 and 150 mM NaCl. This composition is stable at −70° C. for at least six months. The composition may be injected intravenously (i.v.) or subcutaneously (s.c.), although it is generally preferable to inject it intramuscularly (i.m.). The individual doses normally used are $10^7$ to $10^8$ c.f.u. (colony forming units of neomycin resistance titered on HT1080 cells). These are administered at one to two week intervals for three or four doses initially. Subsequent booster shots may be given as one or two doses after 6–12 months, and thereafter annually.

Oral formulations may also be employed with carriers or diluents such as cellulose, lactose, mannitol, poly (DL-lactide-co-glycolate) spheres, and/or carbohydrates such as starch. The composition may take the form of, for example, a tablet, gel capsule, pill, solution, or suspension, and additionally may be formulated for sustained release. For rectal administration, preparation of a suppository may be accomplished with traditional carriers such as polyalkalene glucose, or a triglyceride.

The following examples are offered by way of illustration, and not by way of limitation.

EXAMPLES

Example 1

Isolation of ras$^{*12}$

A 700 base pair Hind III fragment containing the entire T24 ras$^{*12}$ coding region is obtained from plasmid HRAS1 (ATCC No. 41000) and ligated into the Hind III site of pSP73 (Promega, Madison, Wis.). This plasmid is designated SP-Val$^{12}$(100) (see FIG. 1). Plasmids containing ras$^{*12}$ may also be obtained from other sources, such as the American Type Culture Collection (Rockville, Md.).

In order to determine proper orientation of ras$^{*12}$ in pSP73, clones are subjected to Pvu II digestion, and a clone containing a 100 bp digest is selected. This clone is designated SP-Val$^{12}$(100).

E. coli (DH5 alpha) (Bethesda Research Labs, Gaithersburg, Md.) is transformed with the SP-Val$^{12}$ vector construct, and propagated to generate a quantity of plasmid DNA. The plasmid is then isolated and purified, essentially as described by Birnboim et al. (*Nuc. Acid Res.* 7:1513, 1979; see also, "Molecular Cloning: A Laboratory Manual," Sambrook et al. (eds.), Cold Spring Harbor Press, p. 1.25 et seq., 1989).

Example 2

Preparation of a vector construct containing Δras$^{*12}$

A. PREPARATION OF ΔRAS$^{*12}$

Figure 2:
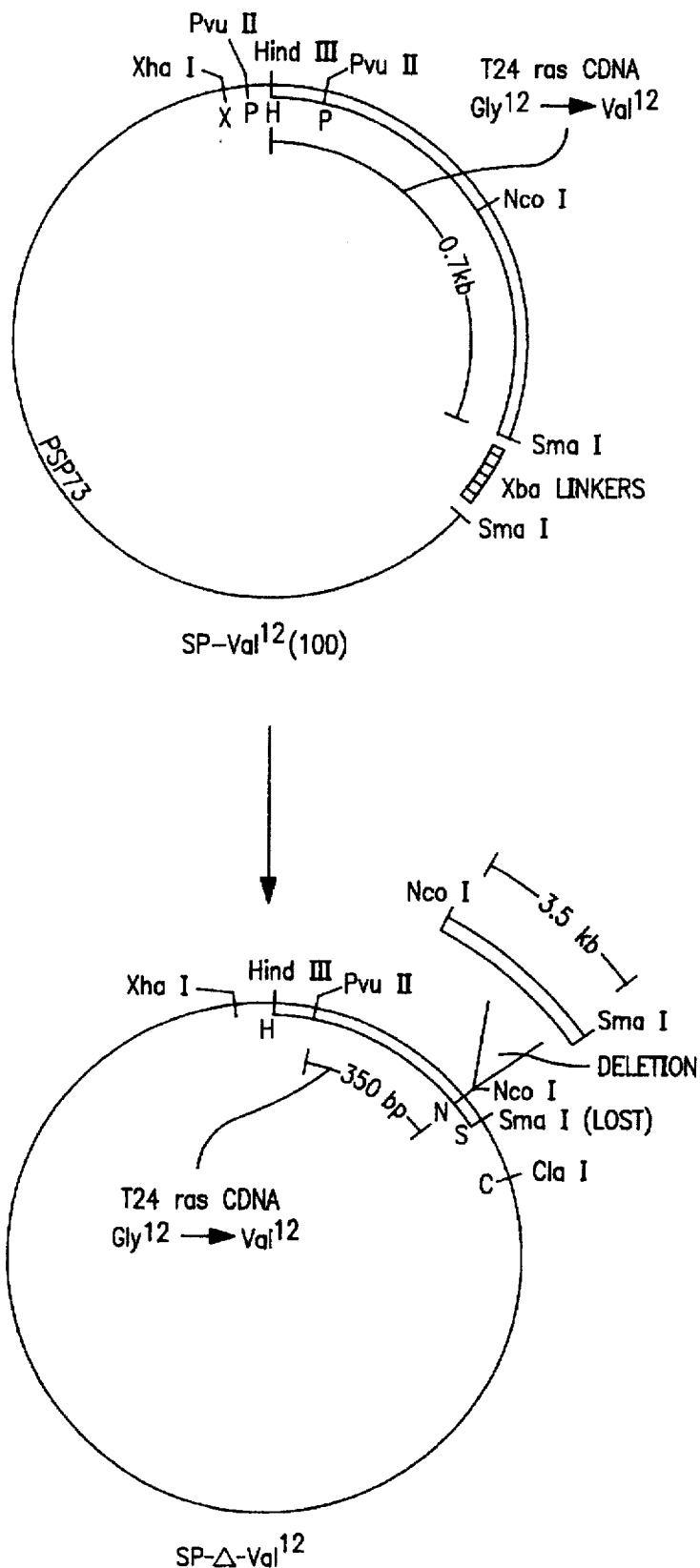
FIG. 2 is a schematic illustration which outlines the construction of the plasmid SP-$\Delta$-Val$^{12}$(100).

A Nco I-Sma I fragment from SP-Val$^{12}$(100) is removed by restriction endonuclease cleavage (see FIG. 2). A Xba I linker (New England Biolabs, Beverly, Mass.) containing a universal stop codon in all three reading flames is inserted 3' to the ras coding sequence. This process forms a poly Xba I region which can be removed by restriction endonuclease cleavage at Xba I sites followed by ligation. This mutant is designated SP-Δ-Val$^{12}$ and expresses non-active truncated ras (ras$^*$) protein.

B. INSERTION OF ΔRAS$^{*12}$ INTO THE RETROVIRAL BACKBONE

N2-ras-neo and N2-ras$^*$-neo retroviral vectors are constructed essentially as described in U.S. Ser. No. 07/586,603. Briefly, this engineered N2 murine recombinant retrovirus contains the SV40 early promoter and the neomycin phosphotransferase gene to facilitate isolation of the infected and transfected cell lines. The N2 Mo MLV gag ATG initiator codon is also altered to ATT by in vitro site-directed mutagenesis in order to increase retroviral titer and enhance the level of expression of transduced genes.

Figure 4:
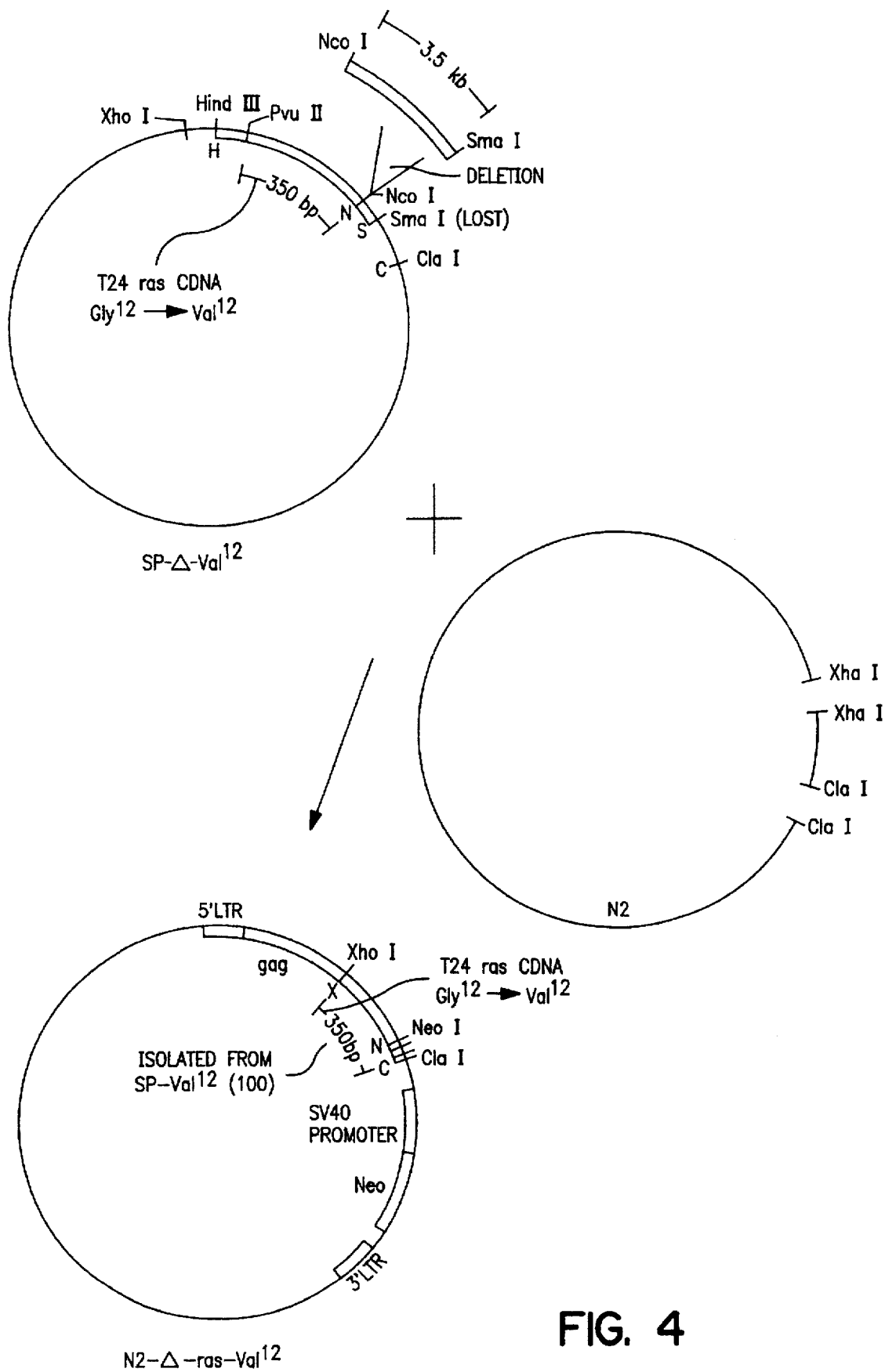
FIG. 4 is a schematic illustration which outlines the construction of the plasmid N2-$\Delta$-ras-Val$^{12}$.
Figure 5:
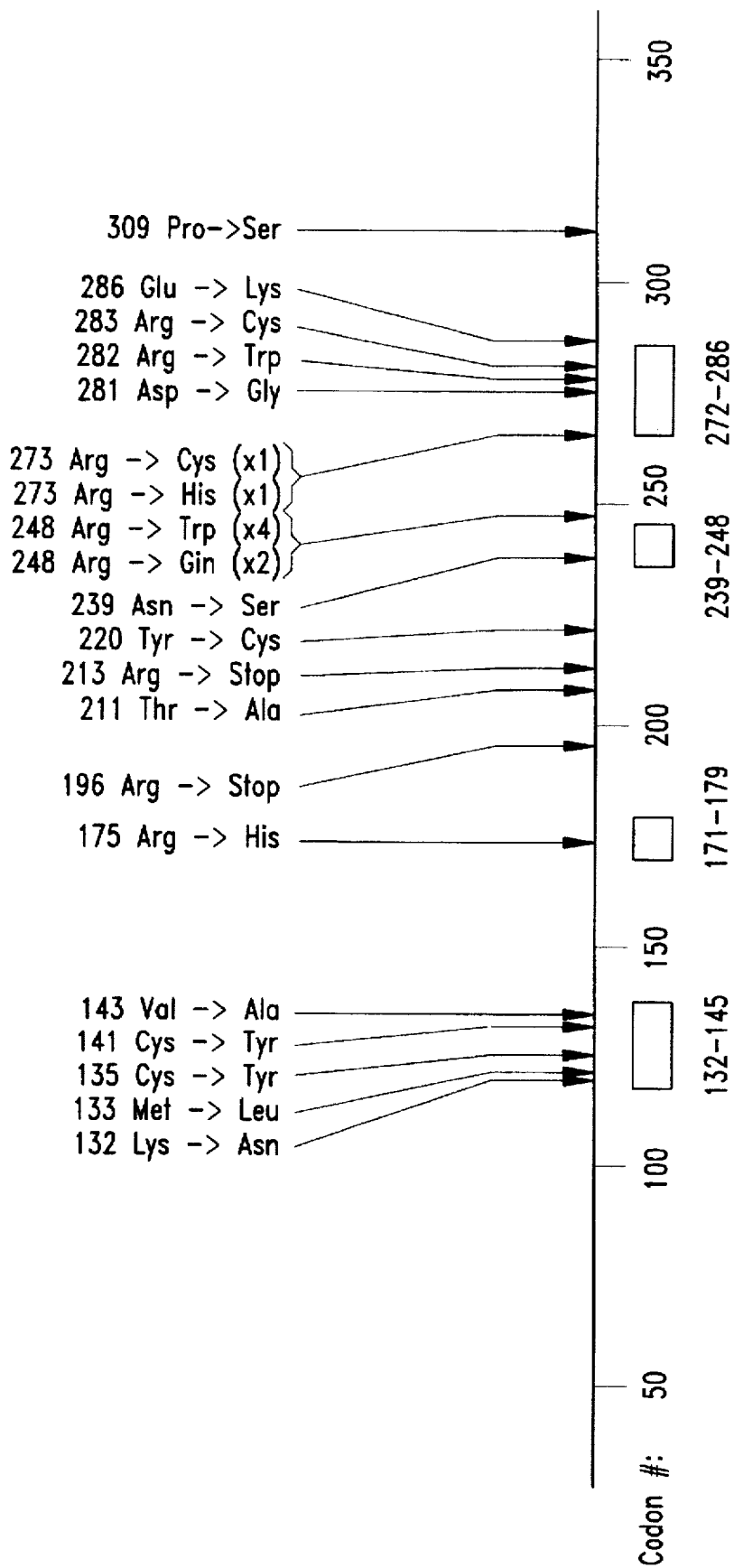
FIG. 5 illustrates four regions of mutations of the p53 gene.

A 350 bp Xho I-Cla I fragment from SP-Δ-Val$^{12}$(100) is then ligated into the retroviral vector. This construct was designated N2-Δ-ras$^*$-Val$^{12}$ (see FIG. 4).

Figure 3:
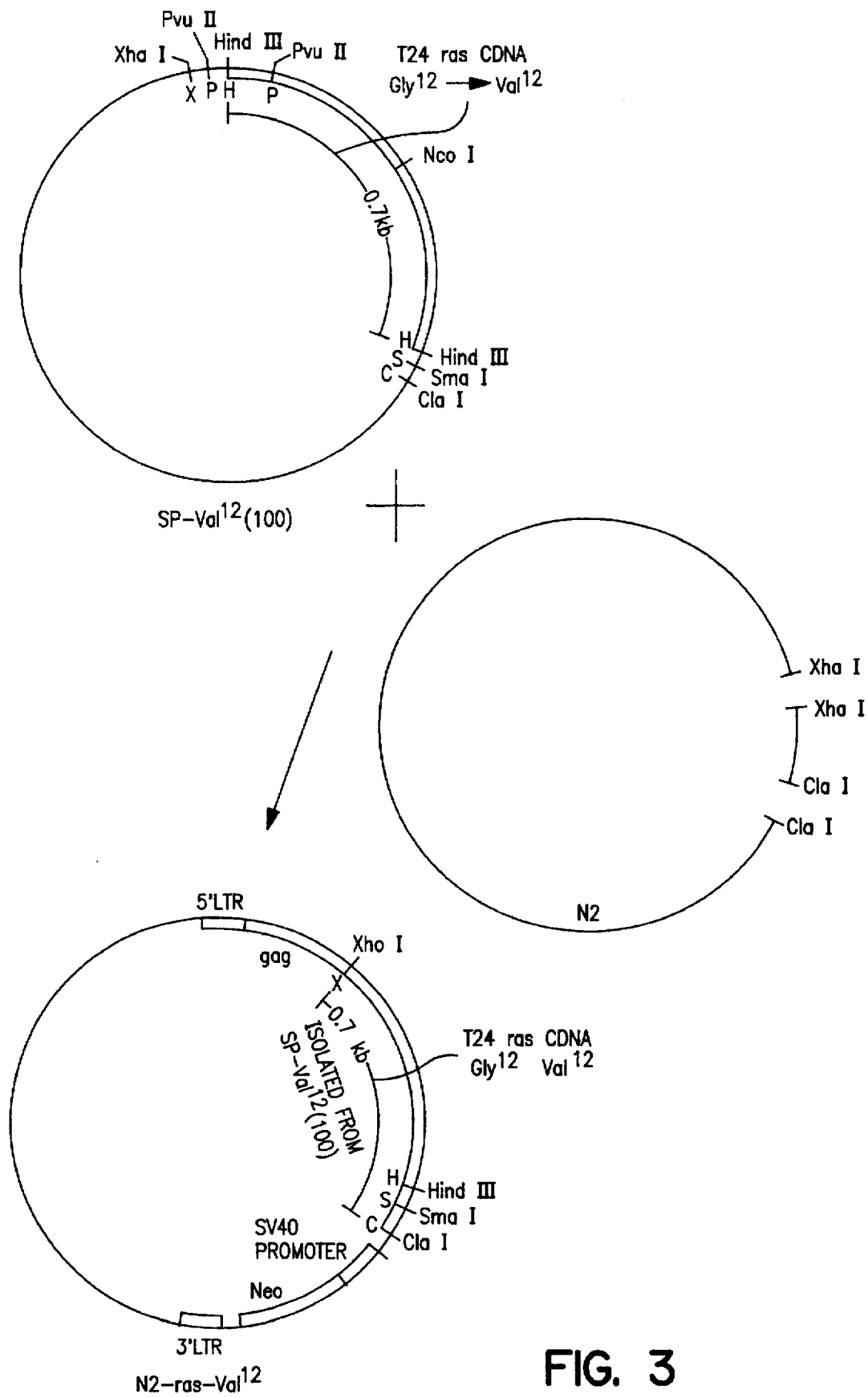
FIG. 3 is a schematic illustration which outlines the construction of the plasmid N2-ras-Val$^{12}$.

The full-length SP-Val$^{12}$(100) cDNA is similarly ligated into the retroviral vector to be used as a positive control for transformation. This construct is designated N2-ras-Val$^{12}$ (see FIG. 3).

Example 3

Transfection of Mammalian Cells

The murine fibroblast cell lines BC10ME (BC, H-2d) and L33 (obtained from Gunther Dennert, University of Southern California), and human fibroblast cell line HT1080 (HT) (ATCC No. CCL 121), are grown in DMEM (Irvine Scientific, Santa Ana, Calif.), containing 10% fetal bovine serum (Gemini, Calabasas, Calif.). BC or HT cells are transduced or transfected with the vector constructs described above. BC-ras$^*$ cells are used for immunization of mice.

Recombinant retrovirus is transfected by the CaPO$_4$ method in CA cells (an amphotropic packaging line) made from the dog cell line CF2; see U.S. Ser. No. 07/586.603). Cells are G418 selected, cloned, and expanded in DMEM supplemented with 10% fetal bovine serum. Viral supernatant from the highest titer clone is filtered with a 0.54 u filter and stored at −70° C.

The mouse fibroblast cell lines BC10M and L33 are transfected with the retroviral vector DNA using the CaPO$_4$ technique and clones are selected using 800 ug/ml G418 for 8 days. Cells are lysed to assay for ras$^*$ protein expression using western blots (see generally Sambrook et al., 18.60 et seq.).

Example 4

Transformation (Tumorigenicity) Assay

Rat 2 cells (ATCC No. CRL 1764) are grown in Dulbecco-Vogt modified Eagle medium supplemented with 10% fetal bovine serum. Rat 2 cells are plated at $10^6$ cells per 5 cm dish 1 day before transfection. The cells are transfected with 0.1–1.0 ug of construct DNA as previously described (Graham and Van Der Eb, 1973; Corsaro and Pearson, 1981). The next day the cells are trypsinized and seeded into three 5 cm dishes and fed every three days thereafter with medium containing 5% fetal bovine serum plus $2\times10^{-6}$M dexamethasone (this enhances the contrast between transformed and non-transformed rat 2 cell morphology). Transformed foci are visible after about 1 week. The plates are stained and foci counted after about three weeks (Miller et al., *Cell* 36:51, 1984).

Cells transfected with ras$^*$ recombinant retroviruses formed transformed foci, whereas those transfected with Δras$^*$ recombinant retroviruses did not.

Example 5

Cytotoxicity Assay

Six- to eight-week- old female BALB/c mice (Harlan Sprague-Dawley, Indianapolis, Ind.) are injected once intraperitoneally (i.p.) with $5\times10^6$ irradiated (10,000 rads, 60°

C.) vector transfected cells (e.g., BC-ras*). Animals are sacrificed 7 days later and the splenocytes ($3\times10^6$/ml) cultured in vitro with irradiated syngeneic transduced cells ($6\times10^4$/ml) in flasks (T-25, Corning, Corning, N.Y.). Culture medium consists of RPMI 1640, heat-inactivated fetal bovine serum (5%, Hyclone, Logan, Utah), sodium pyruvate (1 mM), gentamicin (50 ug/ml) and 2-mercaptoethanol ($10^{-5}$M, Sigma Chemical, St. Louis, Mo.). Effector cells are harvested 4–7 days later and tested using various Effector-:Target cell ratios in 96 well microtiter plates (Corning, Corning, N.Y.) in a standard 4–6 hour assay. The assay employs $Na_2^{51}CrO_4$-labeled (Amersham, Arlington Heights, Ill.) (100 uCi, 1 hr at 37° C.) target cells ($1\times10^4$ cells/well) in a final volume of 200 ul. Following incubation, 100 ul of culture medium is removed and analyzed in a Beckman gamma spectrometer. Spontaneous release (SR) is determined as CPM from targets plus medium and maximum release (MR) is determined as CPM from targets plus 1M HCl. Percent target cell lysis is calculated as: [(Effector cell+target CPM)–(SR)/(MR)–(SR)]×100. Spontaneous release values of targets are typically 10%–20% of the MR.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A recombinant retrovirus directing the cellular expression an immunogenic form of an activated ras protein, wherein said immunogenic activated ras protein has a mutation in one or more of codons 12, 13, 59, 61, 63, 116, 117 or 119, and wherein said immunogenic activated ras protein has been altered to a non-tumorigenic form which does not cause cellular transformation.

2. The recombinant retrovirus of claim 1 wherein said activated ras protein contains a mutation in codon 12 of the ras gene.

3. The recombinant retrovirus of claim 2 wherein said mutation is a point mutation resulting in the conversion of glycine to valine.

4. The recombinant retrovirus of claim 2 wherein said mutation is a point mutation resulting in the conversion of glycine to an amino acid selected from the group consisting of arginine, aspartate, cysteine, alanine, serine, and phenylalanine.

5. The recombinant retrovirus of claim 1 wherein said activated ras protein contains a mutation in codon 13 of the ras gene.

6. The recombinant retrovirus of claim 5 wherein said mutation is a point mutation resulting in the conversion of glycine to an amino acid selected from the group consisting of valine, aspartate and arginine.

7. The recombinant retrovirus of claim 1 wherein said activated ras protein contains a mutation in codon 61 of the ras gene.

8. The recombinant retrovirus of claim 7 wherein said tumorigenic mutation is a point mutation resulting in the conversion of glutamine to an amino acid selected from the group consisting of arginine, histidine, and leucine.

9. The recombinant retrovirus of claim 1 wherein said ras protein is altered to a non-tumorigenic form by truncation.

10. The recombinant retrovirus of claim 9 wherein said truncated ras protein is encoded by SP-Δ-Val$^{12}$.

11. Ex vivo cells infected with a recombinant retrovirus expressing an immunogenic form of an activated ras protein, wherein said immunogenic activated ras protein has a mutation in one or more of codons 12, 13, 59, 61, 63, 116, 117 or 119, and wherein said immunogenic activated ras protein has been altered to a non-tumorigenic form which does not cause cellular transformation.

12. The infected target cell of claim 11 wherein said activated ras protein contains a mutation in codon 12 of the ras gene.

13. The infected target cell of claim 12 wherein said mutation is a point mutation resulting in the conversion of glycine to valine.

14. The infected target cell of claim 12 wherein said mutation is a point mutation resulting in the conversion of glycine to an amino acid selected from the group consisting of arginine, aspartate, cysteine, alanine, serine, and phenylalanine.

15. The infected target cell of claim 11 wherein said activated ras protein contains a mutation in codon 13 of the ras gene.

16. The infected target cell of claim 15 wherein said mutation is a point mutation resulting in the conversion of glycine to an amino acid selected from the group consisting of valine, aspartate and arginine.

17. The infected target cell of claim 11 wherein said activated ras protein contains a mutation in codon 61 of the ras gene.

18. The infected target cell of claim 17 wherein said mutation is a point mutation resulting in the conversion of glutamine to an amino acid selected from the group consisting of arginine, histidine, and leucine.

19. The infected target cell of claim 11 wherein said ras protein is altered to a non-tumorigenic form by truncation.

20. The infected target cell of claim 19 wherein said target cell is infected by a recombinant retrovirus expressing SP-Δ-Val$^{12}$.

* * * * *